US012702344B2

(12) United States Patent
Rajagopal et al.

(10) Patent No.: US 12,702,344 B2
(45) Date of Patent: Aug. 11, 2026

(54) CARDIAC SIGNAL QT INTERVAL DETECTION

(71) Applicant: Medtronic, Inc., Minneapolis, MN (US)

(72) Inventors: Gautham Rajagopal, Minneapolis, MN (US); Shantanu Sarkar, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 268 days.

(21) Appl. No.: 18/538,473

(22) Filed: Dec. 13, 2023

(65) Prior Publication Data

US 2024/0206798 A1 Jun. 27, 2024

Related U.S. Application Data

(63) Continuation of application No. 18/164,759, filed on Feb. 6, 2023, now Pat. No. 11,918,367, which is a (Continued)

(51) Int. Cl.

*A61B 5/352* (2021.01)
*A61B 5/00* (2006.01)

(Continued)

(52) U.S. Cl.

CPC .............. *A61B 5/352* (2021.01); *A61B 5/355* (2021.01); *A61B 5/36* (2021.01); *A61B 5/7203* (2013.01); *A61B 2560/02* (2013.01)

(58) Field of Classification Search

CPC ........... A61B 5/352; A61B 5/355; A61B 5/36; A61B 5/7203; A61B 2560/02;

(Continued)

(56) References Cited

U.S. PATENT DOCUMENTS 5,113,869 A 5/1992 Nappholz et al.
6,721,599 B2 4/2004 de Vries (Continued)

FOREIGN PATENT DOCUMENTS

CN 101057781 A 10/2007
CN 106037720 A 10/2016

(Continued)

OTHER PUBLICATIONS

"D-PO01-NC-09 Development and Validation of a QR Detection Algorithm Designed for Continuous Long-Term Monitoring Using an Insertable Cardiac Monitor," Heart Rhythm, vol. 17, No. 5, May Supplement 2020, 114 pg.

(Continued)

*Primary Examiner* — Carl H Layno
*Assistant Examiner* — Mary Grace Schlueter
(74) *Attorney, Agent, or Firm* — Shumaker & Sieffert, P.A.

(57) ABSTRACT

An example device for detecting one or more parameters of a cardiac signal is disclosed herein. The device includes one or more electrodes and sensing circuitry configured to sense a cardiac signal via the one or more electrodes. The device further includes processing circuitry configured to determine an R-wave of the cardiac signal and determine whether the R-wave is noisy. Based on the R-wave being noisy, the processing circuitry is configured to determine whether the cardiac signal around a determined T-wave is noisy. Based on the cardiac signal around the determined T-wave not (Continued)

being noisy, the processing circuitry is configured to determine a QT interval or a corrected QT interval based on the determined T-wave and the determined R-wave.

21 Claims, 23 Drawing Sheets

Related U.S. Application Data continuation of application No. 17/208,510, filed on Mar. 22, 2021, now Pat. No. 11,576,606.

(60) Provisional application No. 63/004,017, filed on Apr. 2, 2020.

(51) Int. Cl.
*A61B 5/355* (2021.01)
*A61B 5/36* (2021.01)

(58) Field of Classification Search
CPC .... A61B 5/363; A61B 5/7275; A61N 1/3756; A61N 1/3621; A61N 1/3704; A61N 1/37247; A61N 1/37264; A61N 1/37282; G06F 2218/16; G16H 40/63; G16H 50/30
USPC .......................................................... 600/512
See application file for complete search history.

(56) References Cited

U.S. PATENT DOCUMENTS

| | | | |
|---|---|---|---|
| 6,768,919 B2 | 7/2004 | Starobin et al. | |
| 7,027,858 B2 | 4/2006 | Cao et al. | |
| 7,155,282 B1 | 12/2006 | Min et al. | |
| 7,225,015 B1 | 5/2007 | Min et al. | |
| 7,450,986 B2 | 11/2008 | Nguyen et al. | |
| 8,126,539 B2 * | 2/2012 | Zhou | A61B 5/349 607/9 |
| 8,165,664 B1 * | 4/2012 | Farazi | A61B 5/4842 600/509 |
| 8,433,395 B1 | 4/2013 | Brockway et al. | |
| 8,571,644 B2 | 10/2013 | Xue et al. | |
| 11,576,606 B2 | 2/2023 | Rajagopal et al. | |
| 11,589,794 B2 | 2/2023 | Rajagopal et al. | |
| 12,004,863 B2 | 6/2024 | Zhang et al. | |
| 2004/0015197 A1 | 1/2004 | Gunderson | |
| 2009/0192398 A1 | 7/2009 | Zhou et al. | |
| 2010/0312131 A1 | 12/2010 | Naware et al. | |
| 2013/0131530 A1 | 5/2013 | Brockway et al. | |
| 2015/0230723 A1 | 8/2015 | Stadler et al. | |
| 2016/0120430 A1 | 5/2016 | Bayasi et al. | |
| 2016/0135708 A1 * | 5/2016 | Chakravarthy | G16H 50/30 600/515 |
| 2016/0213941 A1 | 7/2016 | Zhang | |
| 2016/0246937 A1 | 8/2016 | Dziubinski et al. | |
| 2016/0256063 A1 | 9/2016 | Friedman et al. | |
| 2016/0342827 A1 | 11/2016 | Kaiami et al. | |
| 2018/0207429 A1 * | 7/2018 | Reinke | A61N 1/37211 |
| 2019/0110707 A1 | 4/2019 | Hemming et al. | |
| 2023/0181083 A1 | 6/2023 | Rajagopal et al. | |

FOREIGN PATENT DOCUMENTS

| | | |
|---|---|---|
| CN | 107106066 A | 8/2017 |
| CN | 107205656 A | 9/2017 |
| CN | 108514414 A | 9/2018 |
| CN | 109561844 A | 4/2019 |

OTHER PUBLICATIONS

Al-Khatib et al., "What Clinicians Should Know About the QT Interval," Journal of American Medical Association (JAMA), vol. 289, No. 16, Apr. 2003, 8 pp.
Chouchoulis et al., "Impact of QT Interval Prolongation Following Antiarrhythmic Drug Therapy on Left Ventricular Function," Future Cardiology, vol. 13, No. 1, Dec. 2016, 10 pp.
Cox, N., "The QT Interval: How Long is too Long?," Nursing made Incredibly Easy!, vol. 9, No. 2, Mar. 2011, 4 pp.
De Bruyne et al., "QTc Dispersion Predicts Cardiac Mortality in the Elderly: The Rotterdam Study," Circulation, vol. 97, No. 5, Feb. 1998, 13 pp.
HRS2020Science Online Abstract entitled "D-PO01-NC-09 Development and Validation of a QT Detection Algorithm Designed for Continuous Long-term Monitoring Using An Insertable Cardiac Monitor," retrieved from https://cslide-us.ctimeetingtech.com/hrs20/attendee/eposter/file/312#1 on Jun. 24, 2021, 2 pp.
International Search Report and Written Opinion of International Application No. PCT/US2021/023582, mailed May 27, 2021, 10 pp.
International Search Report and Written Opinion of International Application No. PCT/US2021/023584, mailed May 27, 2021, 8 pp.
Lee et al., "Influence of Autonomic Neuropathy on QTc Interval Lengthening During Hypoglycemia in Type 1 Diabetes," Diabetes, vol. 53, No. 6, Jun. 2004, 8 pp.
Marfella et al., "QTc Dispersion, Hyperglycemia, and Hyperinsulinemia," Circulation, vol. 100, No. 25, Dec. 1999, 2 pp.
Molnar et al., "Diurnal Pattern of QTc Interval: How Long is Prolonged? Possible Relation to Circadian Triggers of Cardiovascular Events," Journal of the American College of Cardiology, vol. 27, No. 1, Jan. 1996, 8 pp.
Morganroth et al., "Evaluation and Management of Cardiac Safety Using the Electrocardiogram in Oncology Clinical Trials: Focus on Cardiac Repolarization (QTc Interval)," Clinical Pharmacology and Therapeutics, vol. 87, No. 2, Feb. 2010, 9 pp.
Morganroth et al., "Variability of the QT Measurement in Healthy Men, with Implications for Selection of an Abnormal QT Value to Predict Drug Toxicity and Proarrhythmia," The American Journal of Cardiology, vol. 67, No. 8, Apr. 1991, 3 pp.
Postema et al., "The Measurement of the QT Interval," Current Cardiology Reviews, vol. 10, No. 3, Aug. 2014, 8 pp.
Prosecution History from U.S. Appl. No. 17/208,480, now issued U.S. Pat. No. 11,589,794, dated Mar. 31, 2022 through Dec. 14, 2022, 62 pp.
Prosecution History from U.S. Appl. No. 17/208,510, now issued U.S. Pat. No. 11,576,606, dated Jun. 22, 2022 through Dec. 7, 2022, 47 pp.
Prosecution History from U.S. Appl. No. 18/164,759, dated Aug. 1, 2023 through Nov. 7, 2023, 46 pp.
Rossing et al., "Prolonged QTc Interval Predicts Mortality in Patients with Type 1 Diabetes Mellitus," Diabetic Medicine, vol. 18, No. 3, Mar. 2001, 7 pp.
Vandenberk et al., "Which QT Correction Formulae to Use for QT Monitoring?," Journal of the American Heart Association, vol. 5, No. 6, Jun. 2016, 15 pp.
Viskin, S., "Long QT Syndromes and Torsade de Pointes," The Lancet, vol. 354, No. 9190, Nov. 1999, 9 pp.
First Office Action and Search Report, and translation thereof, from counterpart Chinese Application No. 202180025041.4 dated May 27, 2025, 16 pp.
Second Office Action from counterpart Chinese Application No. 202180025030.6 dated Mar. 4, 2026, 8 pp. Translation Attached.

* cited by examiner

CARDIAC SIGNAL QT INTERVAL DETECTION

This application is a continuation of U.S. Pat. No. 11,918,367, issued Mar. 5, 2024 (previously U.S. patent application Ser. No. 18/164,759, filed Feb. 6, 2023), which is a continuation of U.S. patent application Ser. No. 17/208,510, filed Mar. 22, 2021, which claims the benefit of U.S. Provisional Patent Application No. 63/004,017, filed Apr. 2, 2020, the entire content of each of which is incorporated herein by reference.

TECHNICAL FIELD

This disclosure relates to cardiac monitoring and, more particularly, to detection of QT intervals or corrected QT intervals (QTc) in cardiac signals.

BACKGROUND

Cardiac signal analysis may be performed by a variety of devices, such as implantable medical devices (IMDs), insertable cardiac monitors (ICMs) and external devices (e.g., smart watches, fitness monitors, mobile devices, Holter monitors, wearable defibrillators, or the like). For example, devices may be configured to process cardiac signals (e.g., cardiac electrograms (EGMs) and electrocardiograms (ECGs)) sensed by one or more electrodes. Features of cardiac signals may include the P-wave, Q-wave, R-wave, S-wave, QRS-complex, and T-wave. A QT interval is the time from the beginning of the QRS complex to the end of the T-wave. A QTc interval is a QT interval that has been normalized or corrected with respect to a heart rate using a formula. Accurate detection and delineation of features in cardiac signals, such as QT intervals or QTc intervals, may be of importance for monitoring patient health, such as risk of sudden cardiac death.

SUMMARY

In general, this disclosure is directed to devices and techniques for identifying one or more features and/or determining one or more parameters of a cardiac signal (e.g., EGM and/or ECG) of a patient. For example, the disclosure describes techniques for identifying a QT interval or QTc interval, which may enable predicting whether a patient is experiencing or will experience a tachyarrhythmia or other abnormal cardiac rhythm, which may lead to sudden cardiac death. In some examples, an IMD may deliver therapy to the patient to terminate or prevent a predicted tachyarrhythmia.

In one example, a device includes one or more electrodes; sensing circuitry configured to sense a cardiac signal via the one or more electrodes; and processing circuitry configured to: determine an R-wave of the cardiac signal; determine whether the R-wave is noisy; based on the R-wave not being noisy, determine whether the cardiac signal around a determined T-wave is noisy; and based on the cardiac signal around the determined T-wave not being noisy, determine a QT interval or a corrected QT interval based on the determined T-wave and the determined R-wave.

In another example, a method includes determining, by processing circuitry, an R-wave of a cardiac signal; determining, by the processing circuitry, whether the R-wave is noisy; based on the R-wave not being noisy, determining, by the processing circuitry, whether the cardiac signal around a determined T-wave is noisy; and based on the cardiac signal around the determined T-wave not being noisy, determining, by the processing circuitry, a QT interval or a corrected QT interval based on the determined T-wave and the determined R-wave.

In another example, a non-transitory, computer-readable storage medium storing a set of instructions that, when executed, cause a system to: determine an R-wave of the cardiac signal; determine whether the R-wave is noisy; based on the R-wave not being noisy, determine whether the cardiac signal around a determined T-wave is noisy; and based on the cardiac signal around the determined T-wave not being noisy, determine a QT interval or a corrected QT interval based on the determined T-wave and the determined R-wave.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
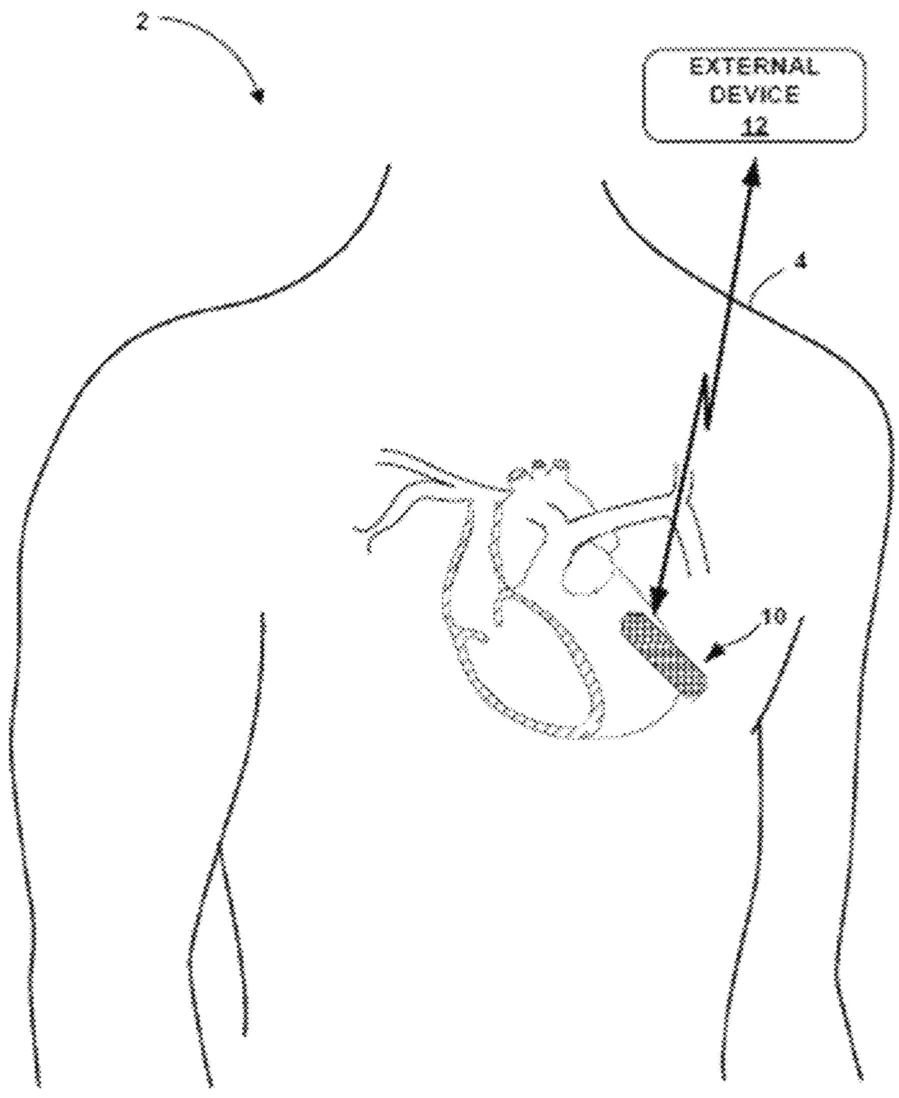
FIG. 1 illustrates the environment of an example medical system in conjunction with a patient.

This disclosure describes techniques for identifying one or more parameters of a cardiac signal, such as QT intervals. The parameters may be used to, for example, detect or predict arrhythmias, to evaluate other conditions of the patient such as change in electrolytes, change in diabetic status, fluid overload or dehydration, or to configure and/or evaluate therapies, such as pharmacological therapies.

A T-wave represents ventricular repolarization. Repolarization of the ventricles begins at the epicardial surface of the ventricles and progresses inwardly through the ventricular walls to the endocardial surface. The T-wave occurs during the last part of the ventricular systole. The onset of the T-wave is the first or abrupt or gradual deviation from the S-T segment. The point where the T-wave returns to the baseline marks the end of the T-wave.

The QT interval on an electrocardiogram (ECG) is measured from the beginning of the QRS complex to the end of the T-wave. The QT interval represents the time it takes for the ventricles of the heart to depolarize and repolarize, or to contract and relax. This electrical activity of the heart is mediated through channels, complex molecular structures within the myocardial cell membrane that regulate the flow of ions in and out of cardiac cells. See, e.g., Viskin S., Long QT Syndromes and Torsade de Pointes, Lancet, Vol. 62(13), pp. 1625-1633, 1999 (hereinafter Viskin). The rapid inflow of positively charged ions (sodium and calcium) results in normal myocardial depolarization. When this inflow is exceeded by outflow of potassium ions, myocardial repolarization occurs. Malfunction of ion channels leads to an intracellular excess of positively charged ions by way of an inadequate outflow of potassium ions or excess inflow of sodium ions. This intracellular excess of positively charged ions extends ventricular repolarization and results in QT interval prolongation. Sec, e.g., Al-Khatib S M, et al., What Clinicians Should Know About the QT Interval, JAMA, Vol. 289(16), pp. 2120-2127, 2003 (hereinafter Al-Khatib).

An abnormally long or abnormally short QT interval is associated with an increased risk of developing abnormal heart rhythms and sudden cardiac death. Abnormalities in the QT interval can be caused by genetic conditions such as Long QT syndrome, by certain medications such as sotalol or pitolisant, by disturbances in the concentrations of certain salts within the blood such as hypokalemia and hypomagnesemia, or by hormonal imbalances such as hypothyroidism, or changes in blood glucose. The normal QT interval varies depending on age and gender, and is usually in the order of about 0.36 to 0.44 seconds. Anything greater than or equal to 0.50 seconds may be considered dangerous for any age or gender. See, e.g., Cox, Natalie K. The QT Interval: How Long is too Long?, Nursing Made Incredibly Easy, Vol. 9(2), pp. 17-21, 2011. The QT interval of an ECG has gained clinical importance, primarily because prolongation of this interval can predispose a person to a potentially fatal ventricular arrhythmia known as torsades de pointes which can lead to sudden cardiac death as discussed in Viskin.

In a clinical setting, it is now widely recognized that a typical measurement of the QT interval is subject to substantial variability, which can cloud interpretation. This variability in QT interval measurement results from biological factors, such as diurnal effects, differences in autonomic tone, electrolytes, and drugs; technical factors, including the environment, the processing of the recording, and the acquisition of the ECG recording; and intra-observer and inter-observer variability, resulting from variations in T-wave morphology, noisy baseline, and the presence of U-waves. Interobserver variability also results from the lack of agreement among experts about standardizing approaches to measure the QT interval. See e.g., Al-Khatib; Morganroth J, et al., Variability of the QT Measurement in Healthy Men, with Implications for Selection of an Abnormal QT Value to Predict Drug Toxicity and Proarrhythmia, American Journal of Cardiology, Vol. 67(8), pp. 774-776, 1991; and Molnar J, et al., Diurnal Pattern of QTc Interval: How Long is Prolonged? Possible Relation to Circadian Triggers of Cardiovascular Events, Journal of the American College of Cardiology, Vol. 27(1), pp. 76-83, 1996.

The QT interval of an ECG has gained clinical importance, primarily because prolongation of this interval can predispose a person to a potentially fatal ventricular arrhythmia known as torsades de pointes which could in turn lead to sudden cardiac death. Multiple factors have been implicated in causing QT prolongation and torsades de pointes. Among these, an important risk factor for long QT syndrome is the use of QT prolonging drugs. A QT interval greater than 500 ms has been shown to correlate with higher risk of torsades de pointes as discussed in Al-Khatib.

Morganroth J, et al., Evaluation and Management of Cardiac Safety Using the Electrocardiogram in Oncology Clinical Trials: Focus on Cardiac Repolarization (QTc Interval), Clinical Pharmacology and Therapeutics, Vol 87(2), pp. 166-74, 2010, recommends that a 10- to 20 ms QT corrected (QTc) change be considered clinically relevant and that patients in this range, especially those with QT-related risk factors, be safeguarded with careful ECG assessment during treatment. Based on adequate risk-benefit evaluation, the authors suggest that higher tolerance limits for QTc prolonging effects may be acceptable for oncological drugs as they meet patients' particular medical needs.

Chouchoulis k, et al., Impact of QT Interval Prolongation Following Antiarrhythmic Drug Therapy on Left Ventricular Function, Future Cardiology, Vol 13(1), 2016, assessed whether antiarrhythmic drug-induced QT interval prolongation affects left ventricular function. The study population included 54 patients with symptomatic recent onset atrial fibrillation spontaneously cardioverted to sinus rhythm. Significant QT maximum (QTmax) and QTc interval prolongation was noticed following drug ingestion including Sotalol (from 424±40 ms to 460±57 ms and from 446±35 ms to 474±48 ms, respectively, both p<0.01) and Amiodarone (from 437±41 ms to 504±39 ms and from 469±35 ms to 527±50 ms, respectively, both p<0.01). Thus, significant prolongation of QTc was noticed in this study following antiarrhythmic drugs such as Sotalol and Amiodarone.

Several studies also show a correlation between QT changes and diabetes. Compared to the general population, type 1 diabetes may increase the risk of mortality, due largely to an increased risk of cardiovascular disease. Almost half of patients with type 1 diabetes have a prolonged QTc interval (>440 ms). Diabetes with a prolonged QTc interval was associated with a 29% mortality over 10 years in comparison to 19% with a normal QTc interval according to Rossing P, et al., Prolonged QTc Interval Predicts Mortality in Patients with Type 1 Diabetes Mellitus, Diabetic Medicine, Vol 18 (3), pp. 199-205, 2001.

One study stated that QTc dispersion is an important predictor of cardiac mortality. In a Rotterdam Study (de Bruyne M C, et al., QTc Dispersion Predicts Cardiac Mortality in the Elderly: the Rotterdam Study, Circulation, Vol 97(5), pp. 467-472, 1998), persons in the highest tertile (>60 ms) relative to the lowest tertile (<39 ms) of QTc dispersion had a 2-fold increased risk of cardiac death. The Rotterdam Study also showed that QTc dispersion is larger in diabetic than in nondiabetic persons according to Marfella, et al., QTc Dispersion, Hyperglycemia, and Hyperinsulinemia, Circulation, Vol 100(25), 1999 (hereinafter Marfella).

Marfella evaluated the effect of acute hyperglycemia on QTc duration and QTc dispersion in 27 normal subjects. During glucose clamp administration to the subjects, plasma glucose stabilized at 15 mmol/L, and plasma insulin showed a biphasic pattern of response, with an early rise at 10 minutes (327±89 pmol/L) followed by a gradual and sustained increase (456±120 pmol/L). QTc increased from 413±26 to 442±29 ms (P<0.05) at the end of the clamp administration, and QTc dispersion increased from 32±9 to 55±12 ms (P<0.01). This showed that acute hyperglycemia in normal subjects produces significant increases of QTc and QTc dispersion.

Lee S P, et al., Influence of Autonomic Neuropathy on QTc Interval Lengthening During Hypoglycemia in Type 1 Diabetes, Diabetes, Vol. 53(6), pp. 1535-42, 2004 discussed a study with 28 adults with type 1 diabetes and 8 nondiabetic control subjects. QTc was then measured during controlled hypoglycemia (2.5 mmol/l) using a hyperinsulinemic clamp. Mean (+/−SE) QTc lengthened from 377+/−9 ms (baseline) to a maximum during hypoglycemia of 439+/−13 ms in diabetic participants (BRS+ subjects) and from 378+/−5 to 439+/−10 ms in control subjects. This study showed that hypoglycemia produces electrocardiographic QTc lengthening, a predictor of arrhythmia risk and sudden death.

Thus, continuous monitoring of QT intervals may allow identification of long QT intervals, which may indicate a need for medical intervention. In some examples, continuous monitoring of QT intervals may be performed using an insertable cardiac monitor (ICM). This disclosure describes an example algorithm which may monitor the QT interval with an ICM, such as a LINQ™ ICM by Medtronic plc, of Dublin, Ireland.

A variety of types of medical devices sense cardiac EGMs. Some medical devices that sense cardiac EGMs are non-invasive, e.g., using a plurality of electrodes placed in contact with external portions of the patient, such as at various locations on the skin of the patient. The electrodes used to monitor the cardiac EGM in these non-invasive processes may be attached to the patient using an adhesive, strap, belt, or vest, as examples, and electrically coupled to a monitoring device, such as an electrocardiograph, Holter monitor, or other electronic device. The electrodes are configured to sense electrical signals associated with the electrical activity of the heart or other cardiac tissue of the patient, and to provide these sensed electrical signals to the electronic device for further processing and/or display of the electrical signals. The non-invasive devices and methods may be utilized on a temporary basis, for example to monitor a patient during a clinical visit, such as during a doctor's appointment, or for example for a predetermined period of time, for example for one day (twenty-four hours), or for a period of several days.

External devices that may be used to non-invasively sense and monitor cardiac EGMs include wearable devices with electrodes configured to contact the skin of the patient, such as patches, watches, or necklaces. One example of a wearable physiological monitor configured to sense a cardiac EGM is the SEEQ™ Mobile Cardiac Telemetry System, available from Medtronic plc, of Dublin, Ireland. Such external devices may facilitate relatively longer-term monitoring of patients during normal daily activities, and may periodically transmit collected data to a network service, such as the Medtronic Carelink™ Network.

Some implantable medical devices (IMDs) also sense and monitor cardiac EGMs. The electrodes used by IMDs to sense cardiac EGMs are typically integrated with a housing of the IMD and/or coupled to the IMD via one or more elongated leads. Example IMDs that monitor cardiac EGMs include pacemakers and implantable cardioverter-defibrillators, which may be coupled to intravascular or extravascular leads, as well as pacemakers with housings configured for implantation within the heart, which may be leadless. An example of pacemaker configured for intracardiac implantation is the Micra™ Transcatheter Pacing System, available from Medtronic plc. Some IMDs that do not provide therapy, e.g., implantable patient monitors, sense cardiac EGMs. One example of such an IMD is the LINQ™ ICM, which may be inserted subcutaneously. Such IMDs may facilitate relatively longer-term monitoring of patients during normal daily activities, and may periodically transmit collected data to a network service, such as the Medtronic Carelink™ Network.

While this disclosure discusses techniques for measuring QT intervals with an example ICM, any medical device configured to sense a cardiac EGM via implanted or external electrodes, including the examples identified herein, may implement the techniques of this disclosure for measuring QT intervals. The techniques include evaluation of the cardiac EGM using criteria configured to provide a desired sensitivity and specificity of QT interval detection despite noise and depolarization morphology variations due to varying electrode positions. The techniques of this disclosure for identifying QT intervals may facilitate determinations of cardiac wellness, and risk of sudden cardiac death, and may lead to clinical interventions to suppress the risk of sudden cardiac death.

FIG. 1 illustrates the environment of an example medical system 2 in conjunction with a patient 4, in accordance with one or more techniques of this disclosure. The example techniques may be used with an ICM 10, which may be in wireless communication with at least one of external device 12 and other devices not pictured in FIG. 1. In some examples, ICM 10 is implanted outside of a thoracic cavity of patient 4 (e.g., subcutaneously in the pectoral location illustrated in FIG. 1). ICM 10 may be positioned near the sternum near or just below the level of the heart of patient 4, e.g., at least partially within the cardiac silhouette. ICM 10 includes a plurality of electrodes (not shown in FIG. 1), and is configured to sense a cardiac EGM via the plurality of electrodes. In some examples, ICM 10 takes the form of the LINQ™ ICM, or another ICM similar to, e.g., a version or modification of, the LINQ™ ICM.

External device 12 may be a computing device with a display viewable by the user and an interface for providing input to external device 12 (i.e., a user input mechanism). In some examples, external device 12 may be a notebook computer, tablet computer, workstation, one or more servers, cellular phone, personal digital assistant, or another computing device that may run an application that enables the computing device to interact with ICM 10. External device 12 is configured to communicate with ICM 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies).

External device 12 may be used to configure operational parameters for ICM 10. External device 12 may be used to retrieve data from ICM 10, such as QT intervals. The retrieved data may include values of physiological parameters measured by ICM 10, indications of episodes of arrhythmia or other maladies detected by ICM 10, and physiological signals recorded by ICM 10. For example, external device 12 may retrieve information related to detection of QT intervals by ICM 10, such as a mean, median, minimum, maximum, range or mode of QT intervals over a time period. The time period may be predetermined, for example, hourly, daily or weekly, or may be otherwise based on the timing of the last retrieval of information by external device 12, or may be determined by a user of external device 12, such as by entering a command on external device 12 requesting the information from ICM 10. External device 12 may also retrieve cardiac electrogram (EGM) segments recorded by ICM 10, e.g., due to ICM 10 determining that an episode of arrhythmia or another malady occurred during the segment, or in response to a request to record the segment from patient 4 or another user.

Processing circuitry of medical system 2, e.g., of ICM 10, external device 12, and/or of one or more other computing devices, may be configured to perform the example techniques of this disclosure for determining QT intervals. In some examples, the processing circuitry of medical system 2 may analyze a cardiac EGM sensed by ICM 10 to determine QT intervals in the cardiac EGM. Although described in the context of examples in which ICM 10 that senses the cardiac EGM comprises an insertable cardiac monitor, example systems including one or more implantable or external devices of any type configured to sense a cardiac EGM may be configured to implement the techniques of this disclosure.

Figure 2:
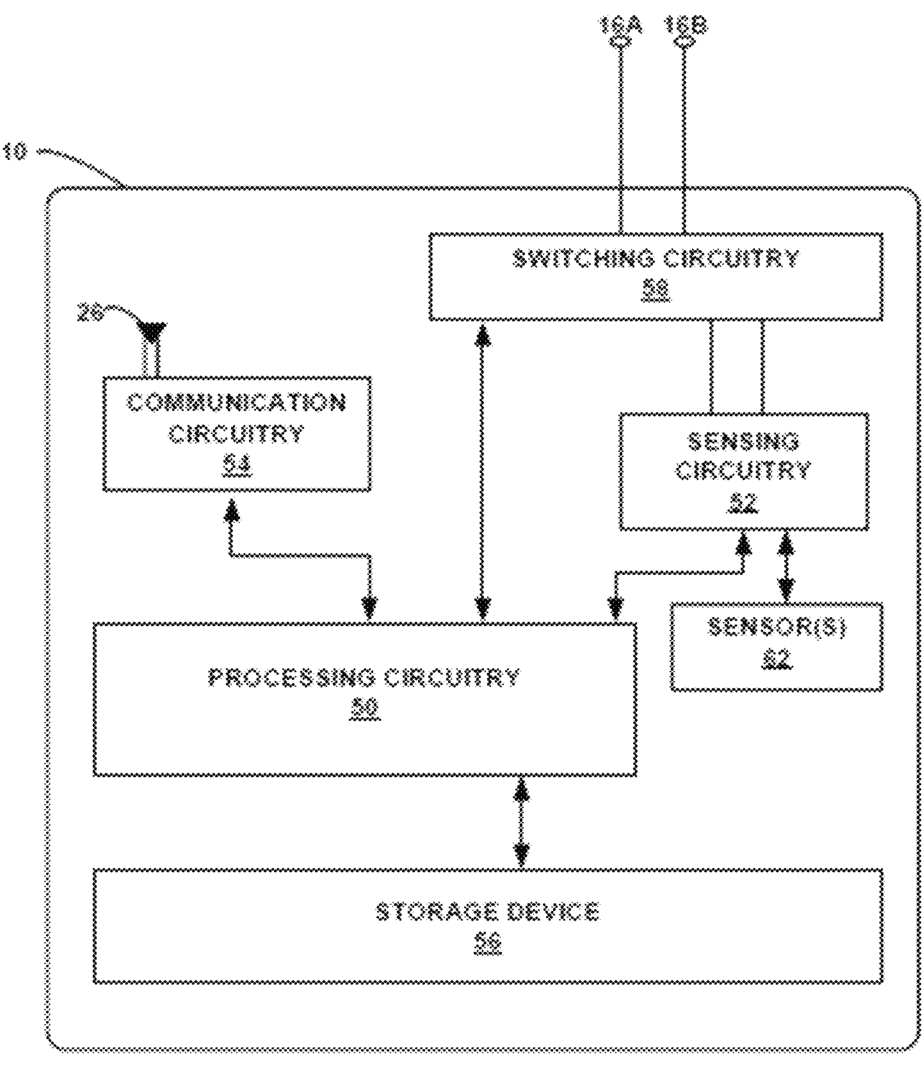
FIG. 2 is a functional block diagram illustrating an example configuration of the insertable cardiac monitor (ICM) of the medical system of FIG. 1.

FIG. 2 is a functional block diagram illustrating an example configuration of ICM 10 of FIG. 1 in accordance with one or more techniques described herein. In the illustrated example, ICM 10 includes electrodes 16A and 16B (collectively "electrodes 16"), antenna 26, processing circuitry 50, sensing circuitry 52, communication circuitry 54, storage device 56, switching circuitry 58, and sensors 62. Although the illustrated example includes two electrodes 16, IMDs including or coupled to more than two electrodes 16 may implement the techniques of this disclosure in some examples.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16 via switching circuitry 58, e.g., to select the electrodes 16 and polarity, referred to as the sensing vector, used to sense a cardiac EGM, as controlled by processing circuitry 50. Sensing circuitry 52 may sense signals from electrodes 16, e.g., to produce a cardiac EGM, in order to facilitate monitoring the electrical activity of the heart. Sensing circuitry 52 also may monitor signals from sensors 62, which may include one or more accelerometers, pressure sensors, and/or optical sensors, as examples. In some examples, sensing circuitry 52 may include one or more filters and amplifiers for filtering and amplifying signals received from electrodes 16 and/or sensors 62.

Sensing circuitry 52 and/or processing circuitry 50 may be configured to detect R-waves and T-waves. Sensing circuitry 52 may include one or more rectifiers, filters, amplifiers, comparators, and/or analog-to-digital converters, in some examples. In some examples, sensing circuitry 52 may output an indication to processing circuitry 50 in response to sensing an R-wave or a T-wave. In some examples, processing circuitry 50 may determine an R-wave or a T-wave in an indication from sensing circuitry 52. Processing circuitry 50 may use the indications of detected R-waves and T-waves for determining QT intervals or corrected QT intervals (QTc).

Sensing circuitry 52 may also provide one or more digitized cardiac EGM signals to processing circuitry 50 for analysis, e.g., for use in cardiac rhythm discrimination, and/or for analysis to determine QT intervals or QTc intervals according to the techniques of this disclosure. In some examples, processing circuitry 50 may store the digitized cardiac EGM in storage device 56. Processing circuitry 50 of ICM 10, and/or processing circuitry of another device that retrieves data from ICM 10, may analyze the cardiac EGM to determine QT intervals or QTc intervals according to the techniques of this disclosure.

Communication circuitry 54 may include any suitable hardware, firmware, software or any combination thereof for communicating with another device, such as external device 12, another networked computing device, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic plc CareLink® Network. Antenna 26 and communication circuitry 54 may be configured to transmit and/or receive signals via inductive coupling, electromagnetic coupling, Near Field Communication (NFC), Radio Frequency (RF) communication, Bluetooth®, WiFi, or other proprietary or non-proprietary wireless communication schemes.

In some examples, storage device 56 includes computer-readable instructions that, when executed by processing circuitry 50, cause ICM 10 and processing circuitry 50 to perform various functions attributed to ICM 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 56 may store, as examples, programmed values for one or more operational parameters of ICM 10 and/or data collected by ICM 10 for transmission to another device using communication circuitry 54. Data stored by storage device 56 and transmitted by communication circuitry 54 to one or more other devices may include premature ventricular contraction (PVC) detection quantifications and/or digitized cardiac EGMs, as examples.

Figure 3:
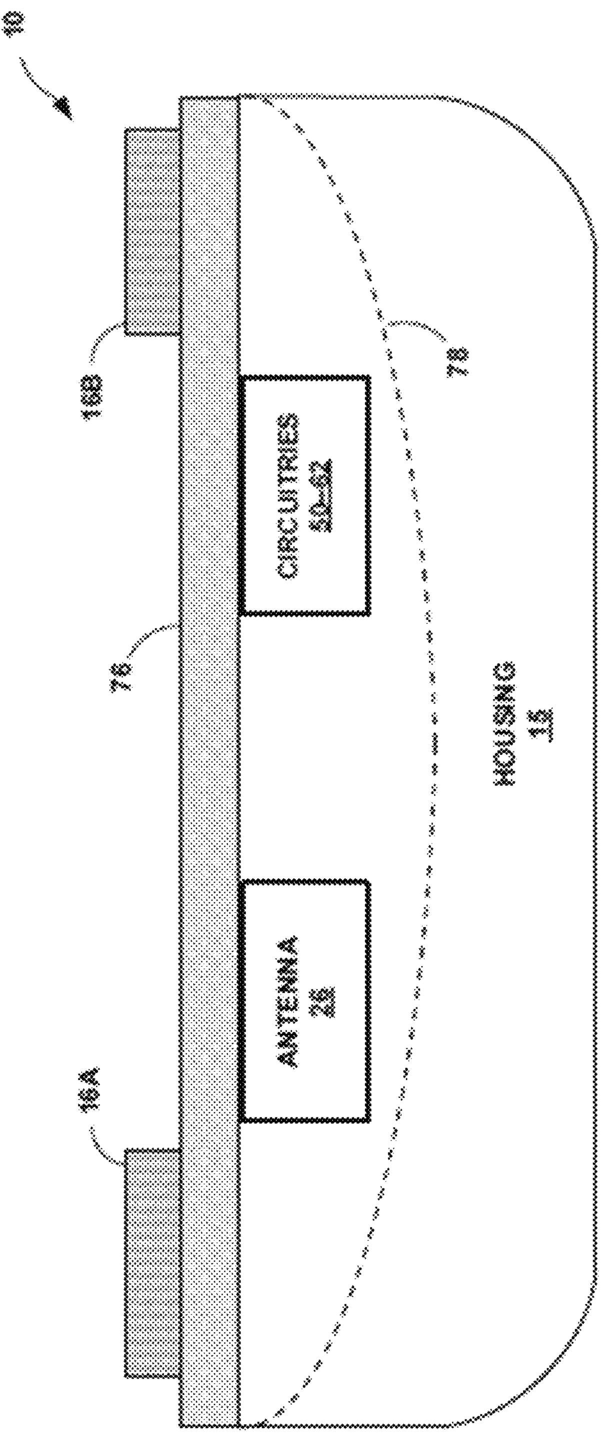
FIG. 3 is a conceptual side-view diagram illustrating an example configuration of the ICM of FIGS. 1 and 2.

FIG. 3 is a conceptual side-view diagram illustrating an example configuration of ICM 10 of FIGS. 1 and 2. In the example shown in FIG. 3, ICM 10 may include a leadless, subcutaneously-implantable monitoring device having a housing 15 and an insulative cover 76. Electrode 16A and electrode 16B may be formed or placed on an outer surface of cover 76. Circuitries 50-62, described above with respect to FIG. 2, may be formed or placed on an inner surface of cover 76, or within housing 15. In the illustrated example, antenna 26 is formed or placed on the inner surface of cover 76, but may be formed or placed on the outer surface in some examples. In some examples, one or more of sensors 62 may be formed or placed on the outer surface of cover 76. In some examples, insulative cover 76 may be positioned over an open housing 15 such that housing 15 and cover 76 enclose antenna 26 and circuitries 50-62, and protect the antenna and circuitries from fluids such as body fluids.

One or more of antenna 26 or circuitries 50-62 may be formed on the inner side of insulative cover 76, such as by using flip-chip technology. Insulative cover 76 may be flipped onto a housing 15. When flipped and placed onto housing 15, the components of ICM 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
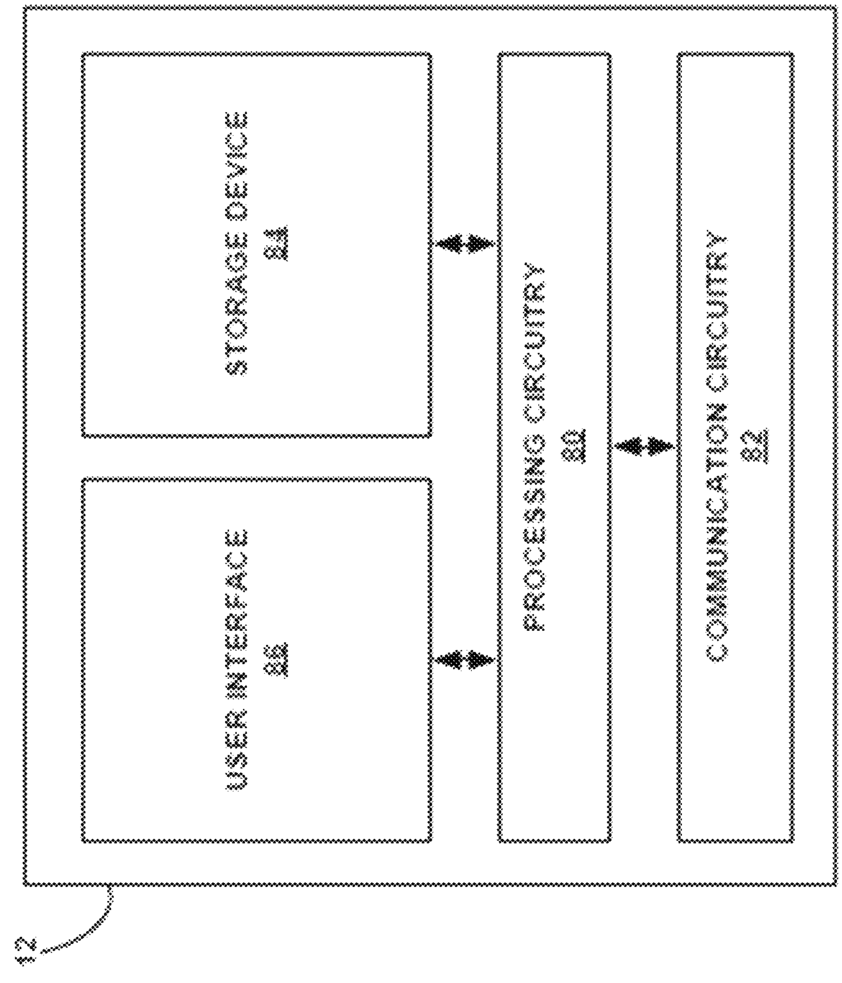
FIG. 4 is a functional block diagram illustrating an example configuration of the external device of FIG. 1.

FIG. 4 is a block diagram illustrating an example configuration of components of external device 12. In the example of FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICS, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as ICM 10. Under the control of processing circuitry 80, communication circuitry 82 may receive downlink telemetry from, as well as send uplink telemetry to, ICM 10, or another device. Communication circuitry 82 may be configured to transmit or receive signals via inductive coupling, electromagnetic coupling, Near Field Communication (NFC), Radio Frequency (RF) communication, Bluetooth®, WiFi, or other proprietary or non-proprietary wireless communication schemes. Communication circuitry 82 may also be configured to communicate with devices other than ICM 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and ICM 10 may include operational parameters. External device 12 may transmit data including computer readable instructions which, when implemented by ICM 10, may control ICM 10 to change one or more operational parameters and/or export collected data, such as QT intervals or QTc intervals. For example, processing circuitry 80 may transmit an instruction to ICM 10 which requests ICM 10 to export collected data (e.g., QT interval data, QTc interval data and/or digitized cardiac EGMs) to external device 12. In turn, external device 12 may receive the collected data from ICM 10 and store the collected data in storage device 84. Processing circuitry 80 may implement any of the techniques described herein to analyze cardiac EGMs received from ICM 10, e.g., to determine QT intervals or QTc intervals.

A user, such as a clinician or patient 4, may interact with external device 12 through user interface 86. User interface 86 includes a display (not shown), such as a liquid crystal display (LCD) or a light emitting diode (LED) display or other type of screen, with which processing circuitry 80 may present information related to ICM 10, e.g., cardiac EGMs, indications of QT intervals or QTc intervals. In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Figure 5A:
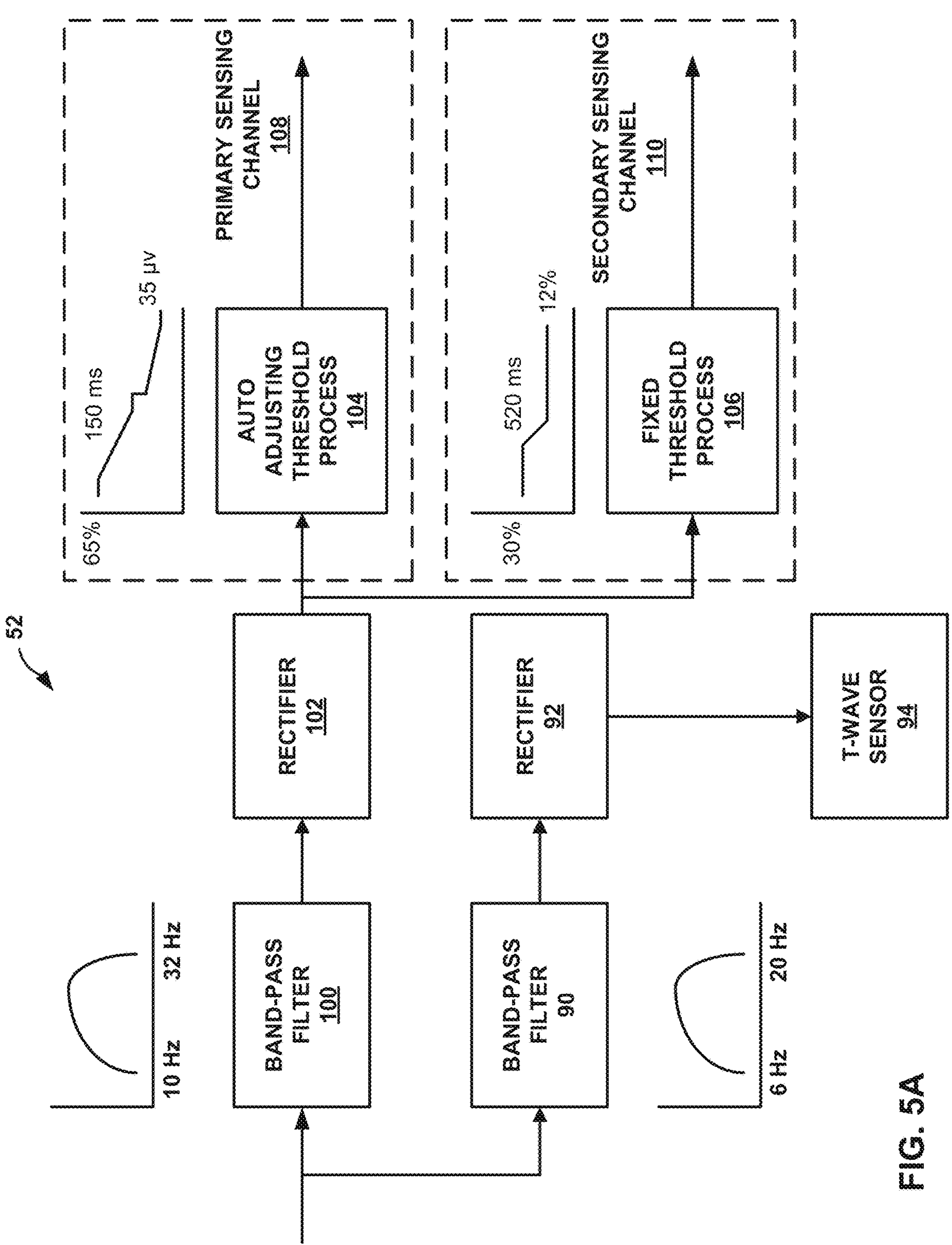
FIGS. 5A and 5B are conceptual diagrams illustrating example primary and secondary sensing channels for an R-wave and a T-wave detector according to the techniques of this disclosure.
Figure 5B:
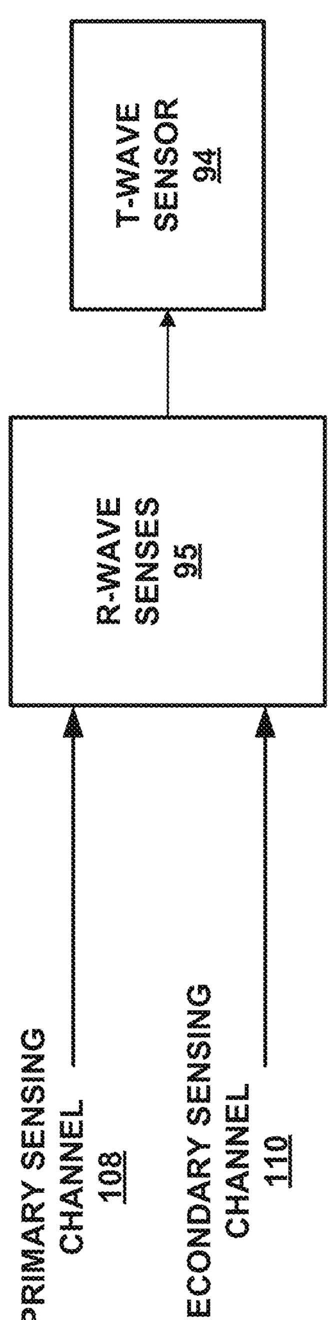

FIGS. 5A and 5B are conceptual diagrams illustrating example primary and secondary sensing channels for R-wave detection and a T-wave detector. In FIG. 5A, sensing circuitry 52 of ICM 10 may sense R-waves by using dual channel sensing techniques of FIGS. 5A and 5B. Cardiac signals (e.g., signals from electrode 16A and electrode 16B) may be filtered by band-pass filter 100. In some examples, band-pass filter 100 may have a passband in the range of about 10 Hz to 32 Hz. In some examples, band-pass filter 100 may have a non-linear response as shown. In other examples, band-pass filter 100 may have a generally linear response. The band-passed signal may then be rectified by rectifier 102.

The rectified signal may then be input to an auto adjusting threshold process 104. For example, auto adjusting threshold process may sense an event has occurred in the cardiac signal when the amplitude of rectified signal from rectifier 102 exceeds the auto adjusted threshold. Auto adjusting threshold process 104 may use an auto adjusting sensitivity with a short blanking period (e.g., in the order of 150 ms). During a blanking period, a sensing process, such as auto adjusting threshold process 104 or fixed threshold process 106, may not sense an event in the cardiac signal so as to avoid a single depolarization from resulting in multiple sensed events. Auto adjusting threshold process 104 may form the primary sensing channel 108, which may be the main R-wave sensing mechanism in ICM 10, and may be configured to accommodate the detection of both tachyarrhythmia and bradyarrhythmia.

Once primary sensing channel 108 detects an R wave, the threshold of auto adjusting threshold process 104 is set at 65% of the amplitude of the detected R wave (which may be a relatively high threshold so that R waves are not detected immediately). Then the threshold decays from the 65% value to 35 microvolt so that the next R wave may be detected. In some examples, there may be points where the threshold drops sharply such as after anticipated T-waves and P-waves to avoid oversensing of T-waves and/or P-waves.

In some examples, the rectified signal may be input into a fixed threshold process 106. Fixed threshold process 106 may have a fixed threshold and a relatively longer blanking period (e.g., in the order of 520 ms) than auto adjusting threshold process 104 to reduce under-sensing. Similar to auto adjusting threshold process 104, fixed threshold process 106 may sense an event in the cardiac signal when the amplitude of the rectified signal exceeds the fixed threshold. The output of fixed threshold process 106 may form a secondary sensing channel 110. In other examples (not shown), secondary sensing channel 110 may use different filtering and/or different rectification than primary sensing channel 108.

The example dual channel sensing scheme of FIGS. 5A and 5B may be employed to avoid under sensing some R-waves, such as those in PVC beats. To capture these beats, a secondary channel, such as secondary sensing channel 110 used with a lower threshold may be used.

For example, when primary sensing channel 108 senses a R-wave, primary sensing channel 108 may blank auto adjusting threshold process 104, as well as the fixed threshold process 106, for a time period, such as 150 ms, to avoid secondary sensing channel 110 from sensing the same beat. If secondary sensing channel 110 senses a R-wave which was not sensed by primary sensing channel 108, secondary sensing channel 110 may blank fixed threshold process 106 for 520 ms after the R-wave sense. In this example, secondary sensing channel 106 may not blank the primary channel from sensing.

To determine the T-wave location, ICM 10 may band-pass the EGM signal, from electrode 16A and electrode 16B, e.g., using band-pass filter 90. In some examples, the band-pass filter may be a 6-20 Hz band-pass filter. The band-passed signal may be rectified by rectifier 92. In FIG. 5B, primary sensing channel 108 and secondary sensing channel 110 determine R-wave senses 95. R-wave senses 95 may be utilized by T-wave sensor 94 to determine a search window for a T-wave.

Figure 6:
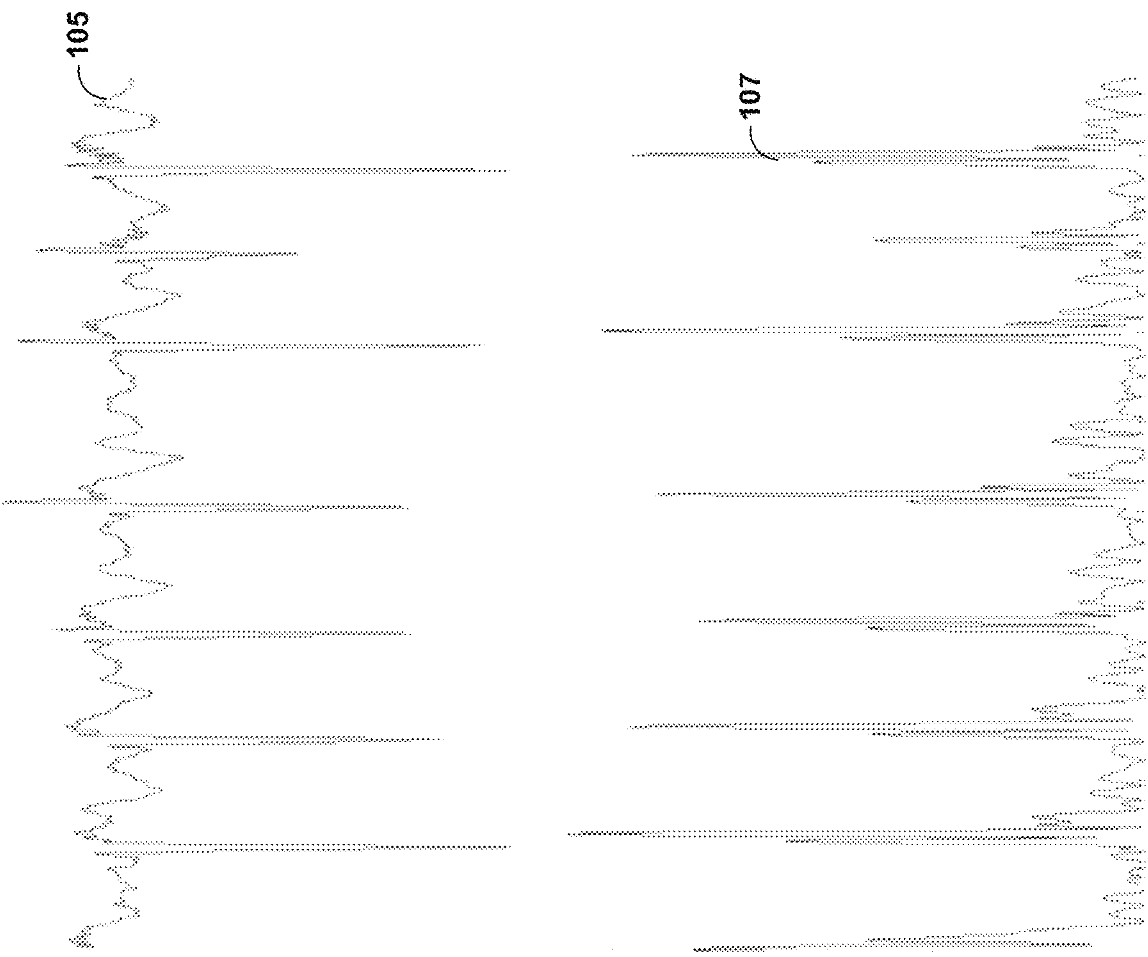
FIG. 6 is a conceptual diagram illustrating an example snippet of an EGM signal and a corresponding rectified waveform.

FIG. 6 is a conceptual diagram illustrating an example snippet of an EGM signal 105 and a corresponding rectified waveform 107.

According to the techniques of this disclosure, ICM 10 may determine the window after the QRS complex to search for the T-wave. ICM 10 may determine the window based on one or more of the current RR interval (the time between two successive R-waves) and the RR interval of the previous beat (the previous RR interval). To accurately determine the starting and ending sample of the search window, ICM 10 may determine the R-wave peak sample in the rectified signal (e.g., in primary sensing channel 108 and/or secondary sensing channel 110). To determine the R-wave peak in the rectified signal, processing circuitry 50 of ICM 10 may take a first predetermined number of samples, such as 14 samples, before the sensed R-wave and a second predetermined number of samples, such as 25 samples, after the sensed R-wave at a predetermined frequency, such as 256 Hz, and determine that the sample with the maximum amplitude is the R-wave peak sample in the rectified signal. In some examples, the first predetermined number of samples and the second predetermined number of samples may be the same. In other examples, the first predetermined number of samples and the second predetermined number of samples may be different. ICM 10 may use this technique to determine the R-wave peak samples of the current, previous and the next beat as parameters peak_current_sample, peak_previous_sample and peak_next_sample, respectively, in order to obtain the current and the previous RR intervals. ICM may determine the R-wave peak samples of the current, previous and next beat to improve the accuracy of the window determination process in which the T-wave location is searched.

After determining the R-wave peak samples, ICM 10 may determine four parameters used for determining the T-wave search window. ICM 10 may determine the parameters of window_start_current and window_end_current based on the current RR interval between the current and the next beat. Similarly, ICM 10 may determine the parameters window_start_previous and window_end_previous based on the previous RR interval between the current beat and previous beat. Table 1 and Table 2 below show examples of the determination of these four parameters based on the current and previous RR interval.

TABLE 1

Determination of window_start_current and window_end_current parameters based on the current RR interval

| Current RR interval (samples at 256 Hz) | Window_start_current parameter | Window_end_current parameter |
|---|---|---|
| <=75 | 27 | 20 |
| >=75 and <=105 | 29 | 25 |
| >105 and <=125 | 40 | 40 |
| >125 and <150 | 45 | 55 |
| >=150 and <170 | 50 | 60 |
| >=170 and <190 | 55 | 65 |
| >=190 and <220 | 55 | 75 |
| >=220 and <240 | 60 | 80 |
| >=240 and <260 | 60 | 85 |
| >=260 and <300 | 70 | 90 |
| >=300 and <350 | 70 | 95 |
| >=350 | 75 | 100 |

TABLE 2

Determination of window_start_previous and window_end_previous parameters based on the current RR interval

| Current RR interval (samples at 256 Hz) | Window_start_current parameter | Window_end_current parameter |
|---|---|---|
| <=75 | 27 | 20 |
| >=75 and <=105 | 29 | 25 |
| >105 and <=125 | 40 | 40 |
| >125 and <150 | 45 | 55 |
| >=150 and <170 | 50 | 60 |
| >=170 and <190 | 55 | 65 |
| >=190 and <220 | 55 | 75 |
| >=220 and <240 | 60 | 80 |
| >=240 and <260 | 60 | 85 |
| >=260 and <300 | 70 | 90 |
| >=300 and <350 | 70 | 95 |
| >=350 | 75 | 100 |

After determining these parameters, the length of the window based on the previous RR interval was determined by:

window_start1 = peak_previous_sample + window_start_previous window_end1 = peak_current_sample − window_end_previous previous_window_length = window_end1 − window_start1

Similarly, the length of the window based on the current RR interval was determined by:

window_start2 = peak_current_sample + window_start_current window_end2 = peak_next_sample − window_end_current current_window_length = window_end2 − window_start2

Figure 7:
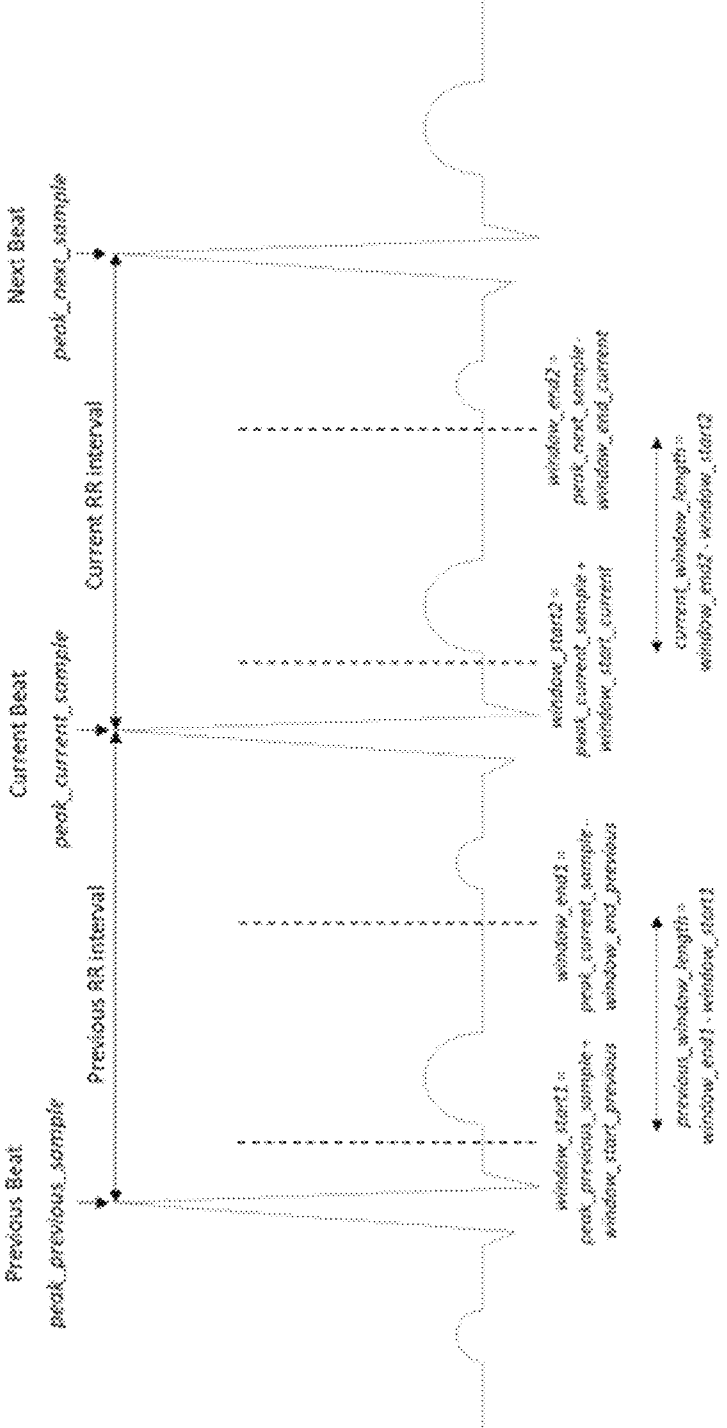
FIG. 7 is a conceptual diagram illustrating an example snippet of an EGM signal depicting the different parameters that may be computed by the QT detection algorithm according to the techniques of this disclosure.

FIG. 7 is a conceptual diagram illustrating an example snippet of an EGM signal depicting the different parameters computed by the QT detection algorithm according to the techniques of this disclosure. In the example of FIG. 7, ICM

10 may determine the starting and ending sample of the search window for the T-wave for the current beat by:

window_start = peak_current_sample + window_start_previous window_end = window_start + previous_window_length.

Figure 8:
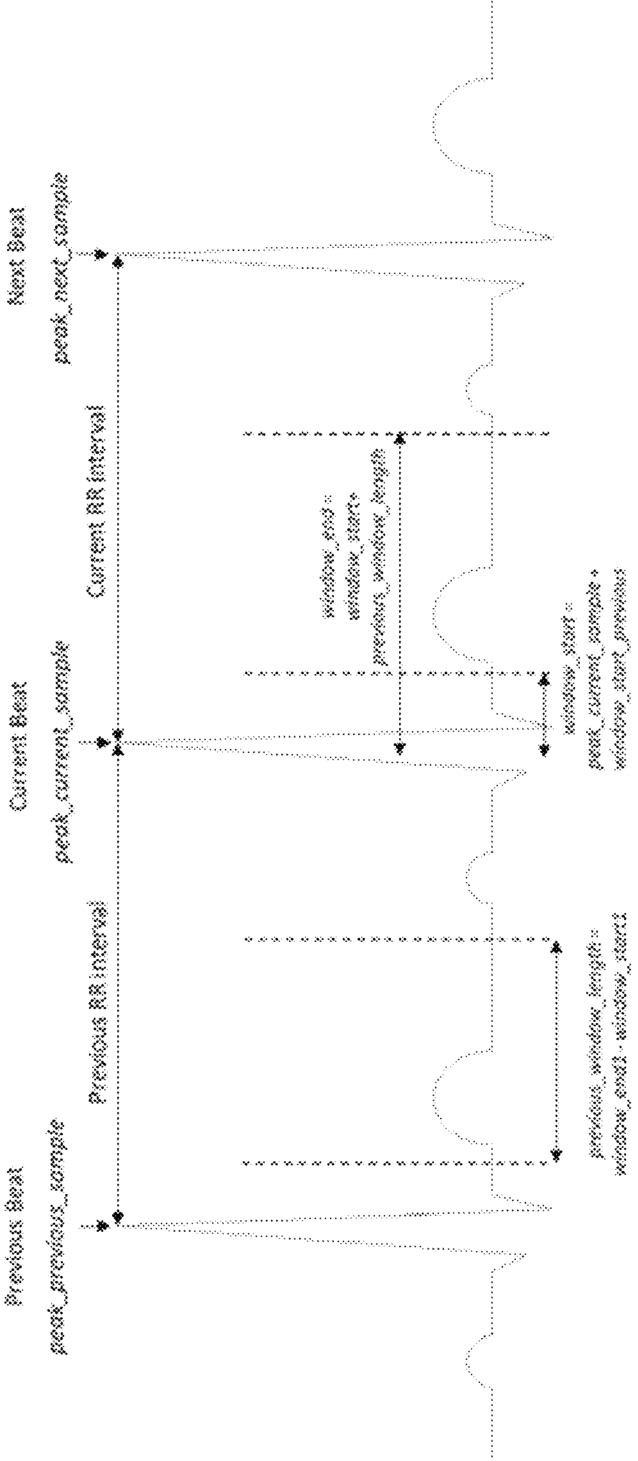
FIG. 8 is a conceptual diagram illustrating an example snippet of an EGM signal depicting the computation of the window_start and window_end parameters according to the techniques of this disclosure.

FIG. 8 is a conceptual diagram illustrating an example snippet of an EGM signal depicting the determination of the window_start and window_end parameters. The starting and ending samples for the search window may be initially determined based on the previous RR interval as shown in FIG. 8. For example, ICM 10 may determine if the condition (window_end>peak_next_sample-a_predetermined_number_of_samples (e.g., 60)) is satisfied, and if the condition is satisfied, ICM may set the parameter window_end to: window_end=window_end2.

ICM 10 may set the parameter window_end=window_end2 to ensure that the P-wave of the next beat is not incorrectly determined to be the T-wave. Thus, if the end of the window as determined using the previous RR interval is close to the QRS complex of the next beat, then the end of the window may be set based on the current RR interval instead of the previous RR interval.

If the difference between the previous and current RR intervals is greater than a third predetermined number of samples, such as a number of samples for example, 128 samples at 256 Hz (500 ms), then ICM 10 may set the window_start and window_end parameters to:

window_start = window_start2 window_end = window_end2

The third predetermined number of samples may be any number of samples, e.g., 102 samples at 256 Hz (400 ms); 154 samples at 256 Hz (600 ms) or 205 samples at 256 Hz (800). In some examples, the frequency may be different than 256 Hz.

Figure 9:
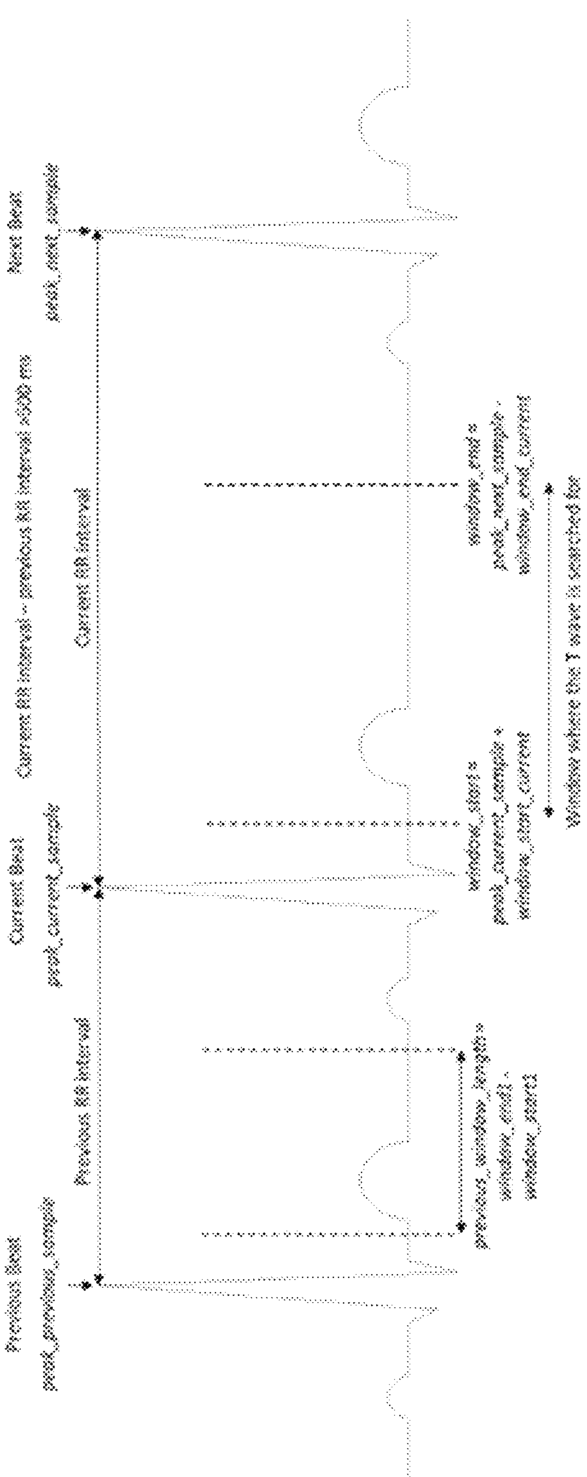
FIG. 9 is a conceptual diagram illustrating an example snippet of and EGM signal depicting the computation of window_start and window_end parameters in the case where the difference between the current and previous RR interval is greater than 500 milliseconds (ms) according to the techniques of this disclosure.

FIG. 9 is a conceptual diagram illustrating an example snippet of an EGM signal depicting the computation of window_start and window_end parameters in the case where the difference between the current and previous RR interval is greater than 500 ms (128 samples at 256 Hz). If the difference between the previous and current RR intervals is greater than the third predetermined number of samples, such as 128 samples (500 ms), then ICM 10 may determine the window start and end samples based on the current RR interval instead of the previous RR interval for accuracy as shown in FIG. 9. Similarly, if the previous beat was determined to be noisy, then ICM 10 may determine the window start and end samples based on the current RR interval instead of the previous RR interval.

ICM 10 may determine the search window for the T-wave to start from the window_start sample and to end at window_end sample. To determine the location of the T-wave, for each sample in the window, a fourth predetermined number of samples, such as a 9-sample median, may be taken (e.g., 4 samples before and 4 samples after a given sample at 256 Hz). ICM 10 may determine the sample with the maximum median value is to be the location of the T-wave. In some examples, ICM 10 may compute the QT interval from the peak_current_sample to this maximum median sample. For example, processing circuitry 50 may determine the QT interval determining a time or a number of samples between peak_current_sample and the maximum median sample.

Normal cardiac repolarization adapts to heart rate. This phenomenon means that with increasing heart rate, the myocardium remains constantly excitable, e.g., completely repolarized, before the next depolarization wave occurs. This prevents incomplete repolarization and the subsequent possibility for re-entrant tachycardia. In Long QT Syndrome, cardiac adaptation to changes in heart rate is disrupted, which promotes arrhythmias. See Postema P G, et al. The Measurement of the QT Interval, Current Cardiology Reviews, Vol 10(3), pp. 287-294, 2014.

The QT interval is dependent on the RR interval and is longer when the heart rate is slower and shorter when the heart rate is faster. So ICM 10 may calculate a corrected QT interval (QTc). Using QTc may improve the detection of patients at increased risk of ventricular arrhythmia. Three methods—Bazett's formula, Fridericia's formula, and Framingham's formula are commonly used to compute QTc intervals:

$$\text{Bazett formula: } QTc = QT/\sqrt{RR}$$

$$\text{Fridericia formula: } QTc = QT/RR^{1/3}$$

$$\text{Framingham formula: } QTc = QT + 0.154(1 - RR)$$

Even though Bazett's formula (logarithmic corrections) is the most commonly used QT correction formula, this formula is not optimal outside of the 60-100 heart rate range. This formula over-corrects at heart rates greater than 100 bpm and under-corrects at heart rates lesser than 60 bpm. Both the Friderica and the Framingham formula perform better for heart rates outside of the 60-100 range. A study showed that the Fridericia and the Framingham correction formulas showed better rate correction and significantly improved prediction of 30-day and 1-year mortality when compared with the Bazett formula. See Vandenberk B, et al., Which QT Correction Formulae to Use for QT Monitoring?, Journal of the American Heart Association, Vol 5(6), 2016. For example, ICM 10 may employ the Framingham formula (a linear correction formula) for computing the QTc interval. In other examples, ICM 10 may employ the Friderica formula. In other examples, ICM 10 may employ the Bazett formula. In other examples, ICM 10 may employ some other formula or techniques to determine the QTc interval. In some examples, ICM 10 may employ more than one of the Framingham formula, the Friderica formula, or the Bazett formula. In such examples, ICM 10 may determine a mean, median or mode QTc based on the formulas used.

A QT detection algorithm which may be implemented in ICM 10 has been developed by using real world clinical data from the de-identified Medtronic plc CareLink™ data warehouse. The algorithm was developed using 74 nightly transmission episodes (each 10 seconds long) from patients with Diabetes and Long QT syndrome and 70 patient activated episodes (30 second EGM snippets) during a follow-up of 1 year from patients implanted with an ICM, such as ICM 10, for the syncope indication in March of 2014 (Reveal LINQ™). The development data set had over 3,800 beats from over 45 patients for analysis. This data set provided T-wave morphologies at different positions and orientations from the ICM.

After extracting the EGM from patient activated episodes, the R-waves were sensed by running an algorithm according to the techniques of this disclosure. The primary and secondary event markers were used to manually annotate the location of T-waves to obtain the manual data. The algorithm results were compared with the manually annotated locations of the T-waves to evaluate the performance of the QT detection algorithm.

Figure 10:
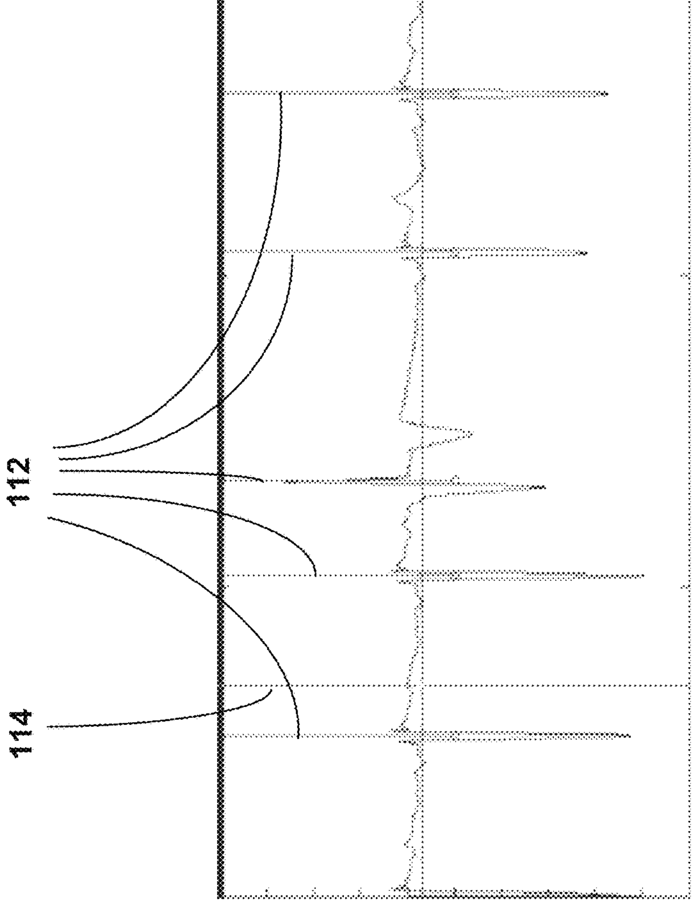
FIG. 10 is a conceptual diagram illustrating an example MATLAB GUI to aid in the manual annotation of a data set.

FIG. 10 is a conceptual diagram illustrating an example GUI to aid in the manual annotation of a data set. The EGM file to be annotated and the markers generated by the algorithm may be input to the GUI. The GUI may display the beats for which the location of the T-waves should be marked by a user. For every R-wave marker 112 displayed on the GUI, the user may select the location of the T-wave 114 by clicking on it. In addition, the user may also assign an annotation to each beat as: 1) a normal beat; 2) a noisy T-wave; or 3) a wrong R-wave marker.

Figure 11:
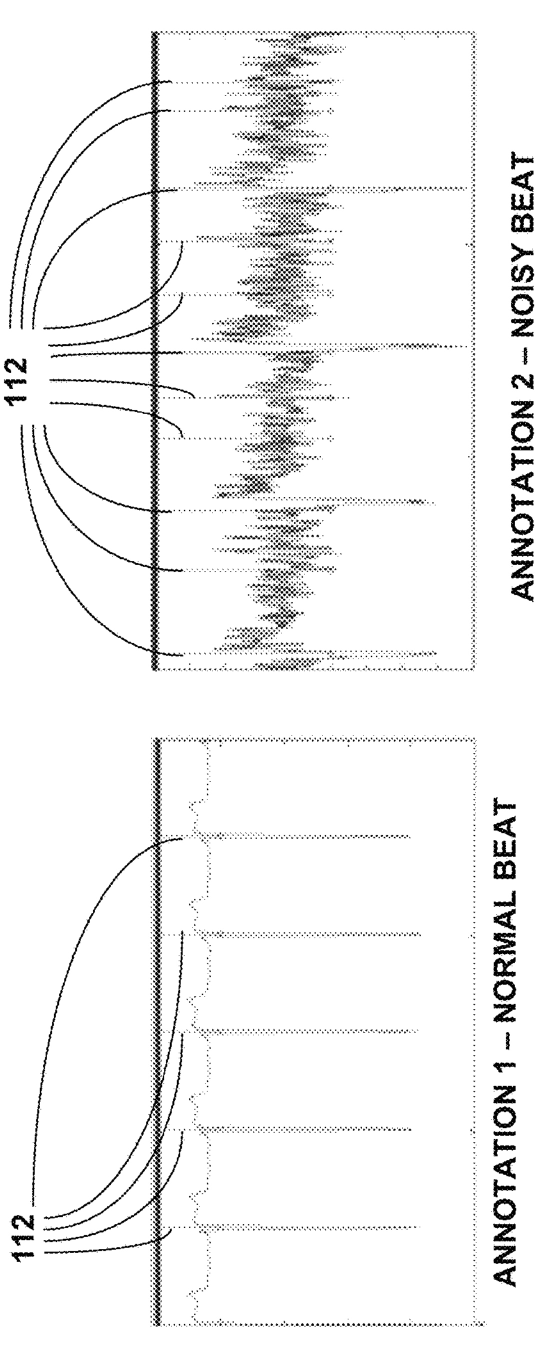
FIG. 11 is a conceptual diagram illustrating examples of manual annotations.
Figure 11:
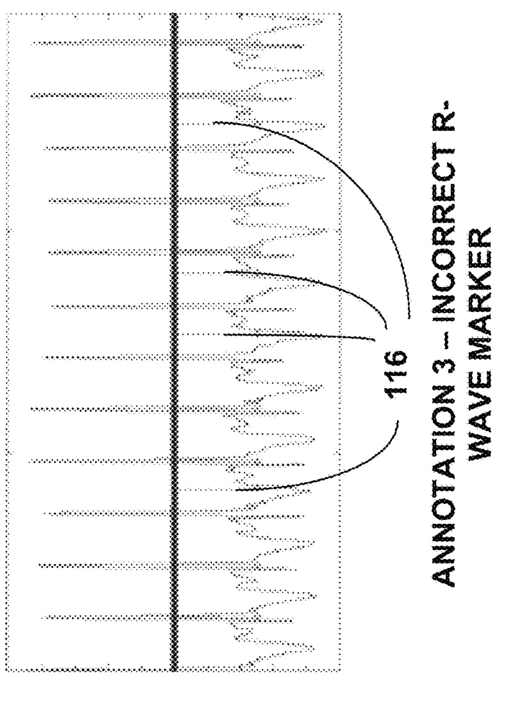

FIG. 11 is a conceptual diagram illustrating examples of manual annotations. After annotating all the R-waves (e.g., adding R-wave markers 112) on the GUI window, the user may press the Enter button to continue to the next set of R-waves that need to be annotated. FIG. 11 shows annotation 1 of a normal beat, annotation 2 of a noisy beat and annotation 3 with incorrect annotations of R-waves 116.

Figure 12:
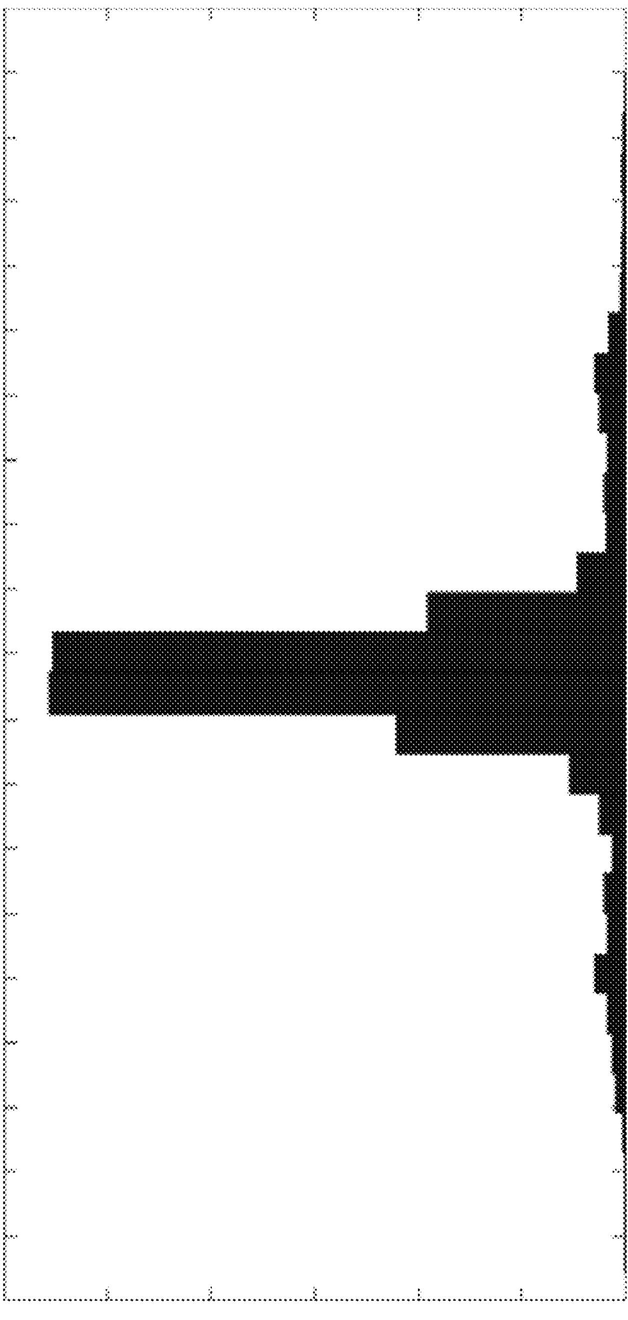
FIG. 12 is a conceptual diagram illustrating a histogram of the difference between the QT interval based on the manual annotations and the QT interval detected results based on the techniques of this disclosure for every beat in a development data set.

FIG. 12 is a conceptual diagram illustrating a histogram of the difference between the QT interval based on the manual annotations and the QT interval computed based on the detected techniques of this disclosure for every beat in the development data set according to techniques of this disclosure. To determine the performance of the QT interval detection techniques of this disclosure, the difference between the QT interval computed based on the manual annotation and the QT interval computed based on the detection techniques of this disclosure (QT(true)–QT(detected)) was computed for every beat in the development data set as shown in FIG. 12. The mean of the absolute value of this parameter was 22.7 ms and the median value was 11.7 ms. The mode was found to be 4 ms. It should be noted that the resolution of QT computation was 4 ms because the EGM data is at 256 Hz.

Table 3 below shows the percentage of beats in the development data corresponding to the absolute value of the parameter (QT(true)–QT(detected)) for every beat in the development data set both in terms of samples and ms where the total number of beats was 3829.

TABLE 3

Percentage of beats in the development data set corresponding to the value of the difference between QT interval based on manual annotation and the QT interval based on the algorithm detection both in terms of ms and the number of samples at 256 Hz.

| | Number of beats | % of beats |
|---|---|---|
| Absolute of (QT(true)-QT(detected)) Samples at 256 Hz | | |
| <=2 | 1778 | 46.4% |
| <=4 | 2603 | 68% |
| <=6 | 2999 | 78.3% |
| <=8 | 3186 | 83.2% |
| <=10 | 3271 | 85.4% |
| <=12 | 3320 | 86.7% |
| Absolute of (QT(true)-QT(detected)) in ms | | |
| <5 | 1106 | 29% |
| <10 | 1778 | 46.4% |
| <15 | 2247 | 58.7% |
| <20 | 2844 | 74.3% |
| <25 | 2999 | 78.3% |

TABLE 3-continued

Percentage of beats in the development data set corresponding to the value of the difference between QT interval based on manual annotation and the QT interval based on the algorithm detection both in terms of ms and the number of samples at 256 Hz.

| | Number of beats | % of beats |
|---|---|---|
| <30 | 3126 | 81.6% |
| <35 | 3186 | 83.2% |
| <40 | 3294 | 86% |

Figure 13:
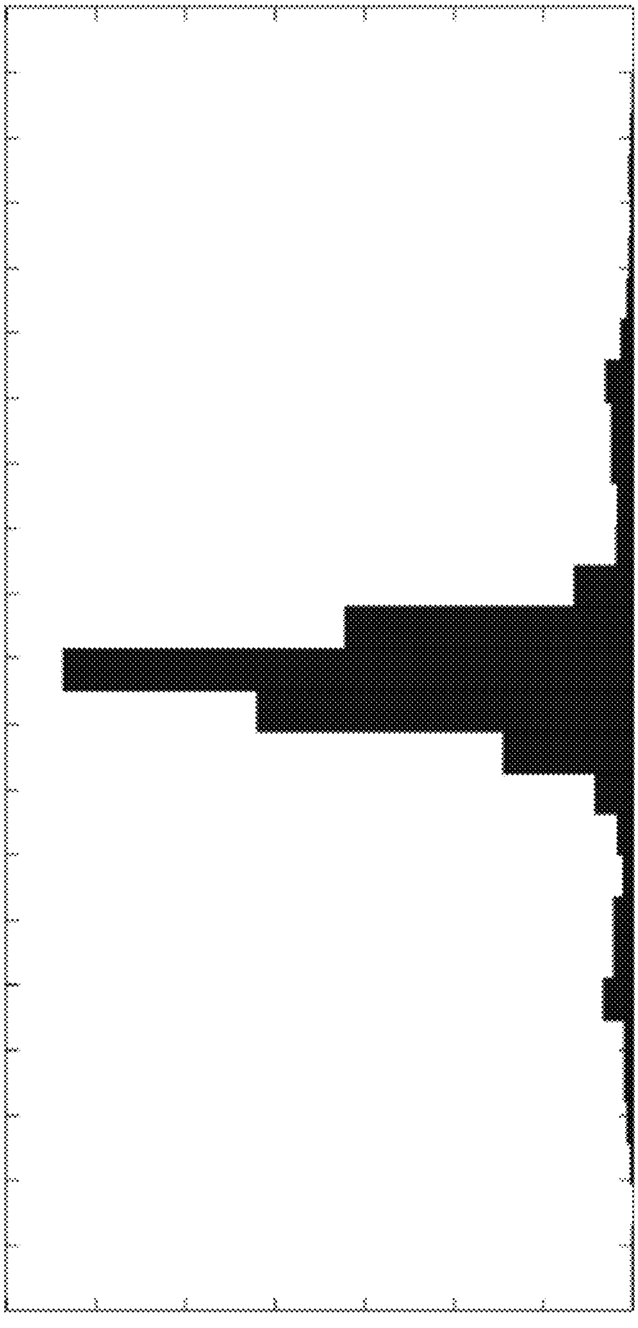
FIG. 13 is a conceptual diagram illustrating a histogram of the difference between the QT corrected (QTc) interval based on the manual annotations and the QTc interval detected results based on the techniques of this disclosure for every beat in the development data set.

FIG. 13 is a conceptual diagram illustrating a histogram of the difference between the QTc interval based on the manual annotations and the QTc interval calculated based on the detection techniques of this disclosure for every beat in the development data set. It can be observed in FIG. 13 and table 4 below that the difference between the QT interval based on manual annotation and the QT interval based on the detection techniques of this disclosure was less than or equal to 2 samples (7.8 ms) for 46.5% of beats in the development data set. This parameter was less than 25 ms for over 78% of the beats in the development data set.

TABLE 4

Percentage of beats in the development data set corresponding to the value of difference between the QTc interval based on manual annotation and the QTc interval based on the algorithm detection in ms.

| Absolute of (QT(true)-QT(detected)) in ms | Number of beats | % of beats |
|---|---|---|
| <5 | 1106 | 29% |
| <10 | 1778 | 46.4% |
| <15 | 2247 | 58.7% |
| <20 | 2712 | 70.8% |
| <25 | 2999 | 78.3% |
| <30 | 3126 | 81.6% |
| <35 | 3187 | 83.2% |
| <45 | 3294 | 86% |

Using the Framingham correction formula, QTc interval was computed for every beat in the development data set. Similar to the example of FIG. 12, the difference between the QTc interval computed based on the manual annotation and the QTc interval based on the detection techniques of this disclosure was computed for every beat in the development data set. The histogram for this parameter is shown in FIG. 13. The mean of the absolute value of this parameter was 22.6 ms and the median value was 12 ms. The mode was found to be 4 ms.

Figure 14:
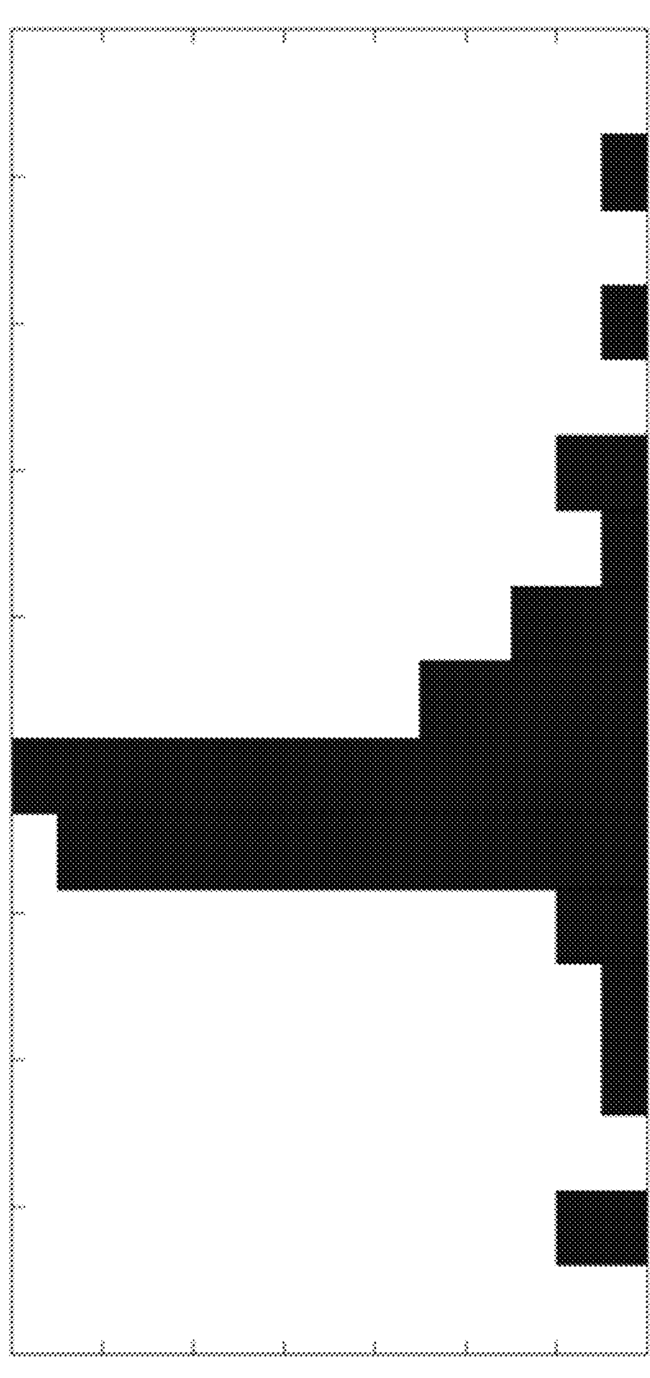
FIG. 14 is a conceptual diagram illustrating a histogram of the mean of the difference between the QTc interval based on the manual annotations and the QTc interval detected results based on the techniques of this disclosure for 46 unique devices in the development data set.

FIG. 14 is a conceptual diagram illustrating a histogram of the mean of the difference between the QTc interval based on the manual annotations and the QTc interval based on the detection techniques of this disclosure for 46 unique devices in the development data set. To determine the performance of the techniques of this disclosure based on unique devices, the parameter of (QTc interval (true)−QT interval (algorithm detected)) was computed for beats in every unique ICM separately and the mean of this parameter was computed for every device. It can be observed in FIG. 14 that 37 out of the 46 devices had a mean of less than 25 ms.

Figures 15A, 15B, 15C, 15D:
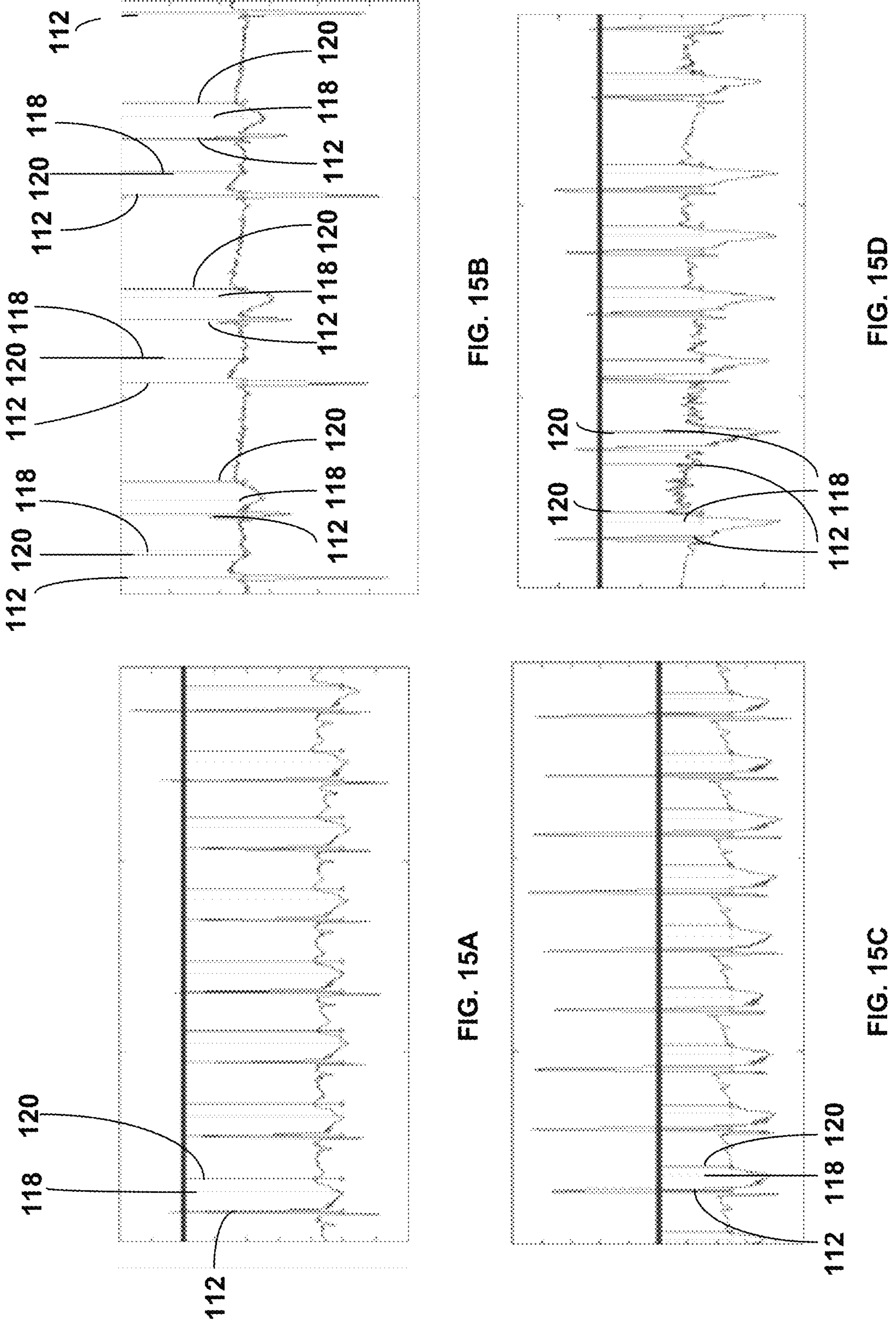
FIGS. 15A-D are conceptual diagrams illustrating example EGM strips from devices for which a mean of (QTc interval(true)−QTc interval(algorithm detected)) was greater than 25 ms depicting both manual annotation and the detections according to the techniques of this disclosure.

FIGS. 15A-D are conceptual diagrams illustrating example devices for which mean of (QTc interval(true)−QTc interval(algorithm detected)) was greater than 25 ms. There were 9 devices which had a mean greater than 25 ms. Some examples from these specific ICMs are shown in FIGS. 15A-D. In several of these ICMs, as shown in FIG. 15A and in some instances in FIG. 15B, the techniques of this disclosure detected T-waves in a different location when compared to the manual annotation, but the T-waves were consistently detected generally in the same location. For example, in FIGS. 15A and 15C, R-wave markers 112 were consistently followed by T-waves 118 determined by manual annotation, followed by T-waves determined according to the detection techniques of the present disclosure 120. This pattern continues throughout FIGS. 15A and 15C. So, changes in QT interval may still be measured in these cases even though the mean of (QTc interval (true)−QTc interval (algorithm detected)) was large in these devices.

In certain ICMs, such as shown in FIG. 15D, there were some variations in detection of T-waves from beat to beat which in some cases was caused due to noise or RR interval variability from beat to beat.

Figure 16:
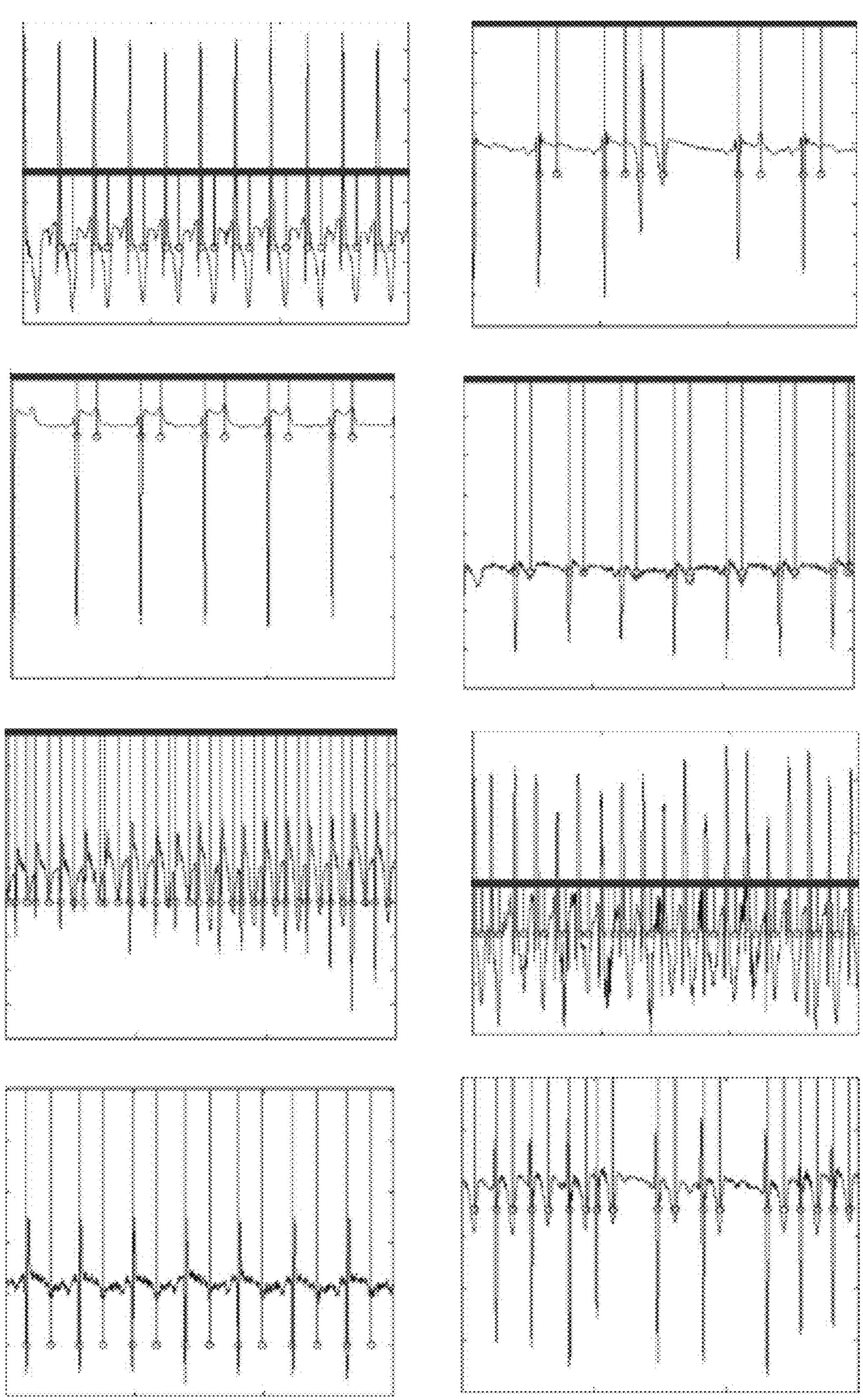
FIG. 16 is a conceptual diagram illustrating example of EGM strips from the development data set having T-waves with different morphologies and orientations at different RR intervals depicting both manual annotation and the detections according to the techniques of this disclosure.

FIG. 16 is a conceptual diagram illustrating example of EGM strips from the development data set having T-waves with different morphologies and orientations at different RR intervals depicting both manual annotation and detections according to the techniques of this disclosure. These examples include both nightly transmissions as well as patient activated episodes from ICMs for which the QT interval was accurately detected by the algorithm.

Figure 17A:
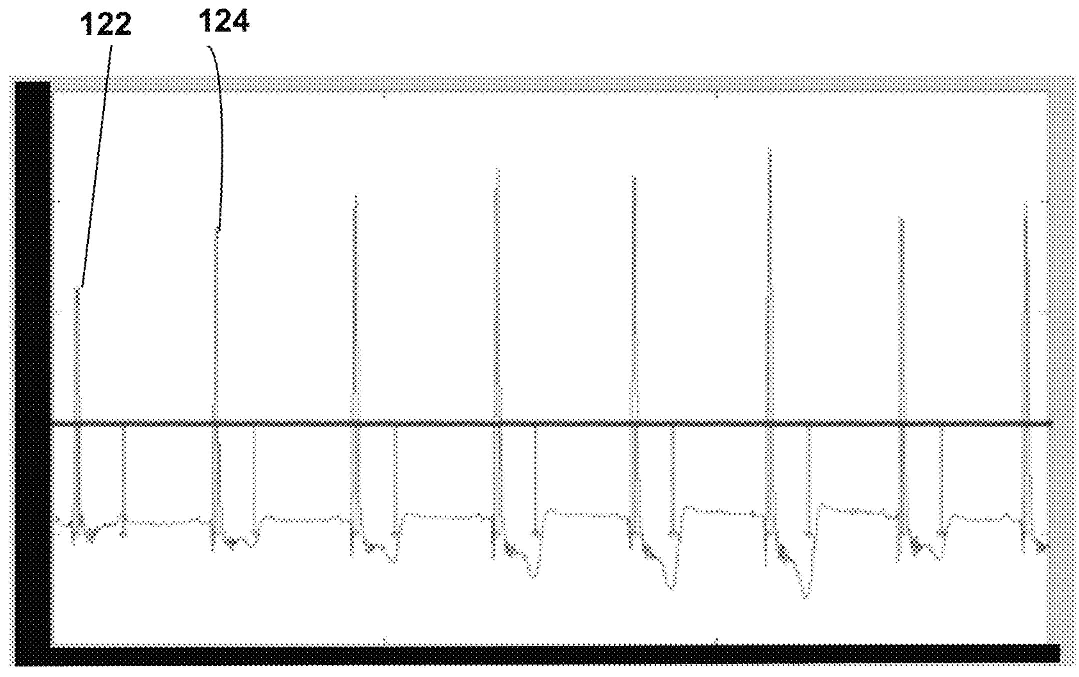
FIG. 17A-B is a conceptual diagram depicting examples of EGM strips from the development data set depicting beat to beat changes in QTc interval detected by both manual annotation as well as detection according to the techniques of this disclosure.
Figure 17B:
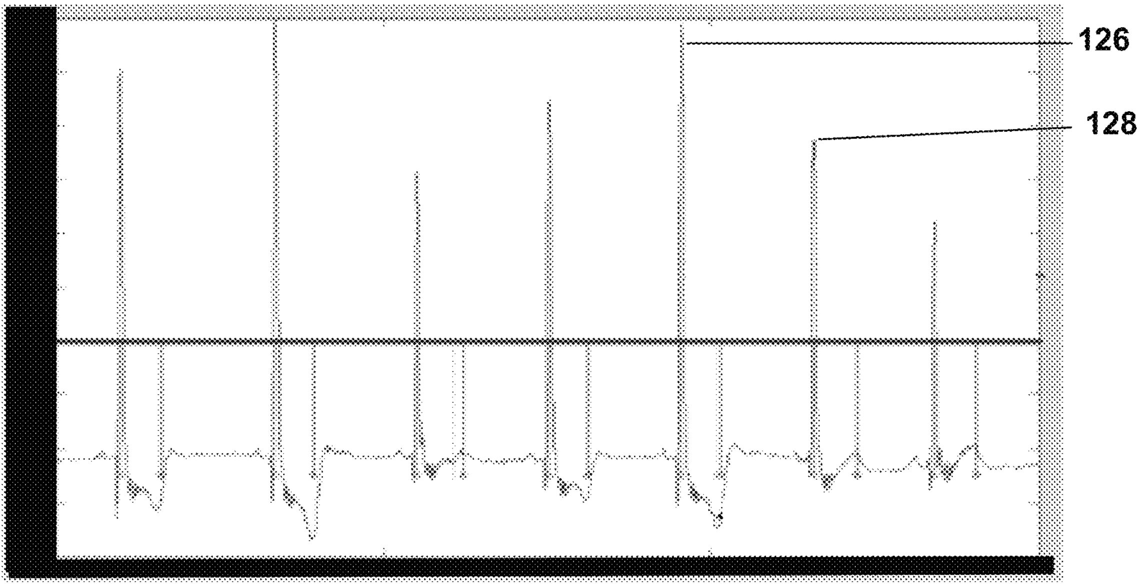

Another observation from the analysis of the development data set was that the ICMs were able to capture beat to beat changes in the QT interval well as shown in FIGS. 17A-B. In FIG. 17A, the QTc changes by 43 ms between beat 122 and beat 124 which was captured well by the ICM. Similarly, in FIG. 17B, the QTc interval changes by 54 ms between beat 126 and beat 128 and changes by 15 ms between beat 128 and the next beat which was captured by ICM 10 as well.

In some examples, the amplitude of the samples in the search window may be weighted by giving more weight to (weighting more heavily) the amplitude of samples located where the T-wave is most likely to be detected based on the previous QT intervals or QTc intervals, such as 12 QT intervals or QTc intervals, and giving less weight to the samples at the end of the window. For example, processing circuitry 50 of ICM 10 may take the last 12 QT intervals or QTc intervals and form a weighting window based on the location of the T-wave in the fastest QT interval or QTc interval and the location of the T-wave in the slowest QT interval or QTc interval and apply a weight to the amplitude of samples inside of the window so that the amplitude of samples is greater than the amplitude otherwise would be. For example, processing circuitry 50 of ICM 10 may apply a weight to the amplitude of samples outside of the window so that the amplitude of samples is less than the amplitude otherwise would be. In some examples, the weighting window may be equal to the location of the T-wave in the fastest QT interval or QTc interval and the location of the T-wave in the slowest QT interval or QTc interval. In other examples, the weighting window may be larger than or smaller than the location of the T-wave in the fastest QT interval or QTc interval and the location of the T-wave in the slowest QT interval or QTc interval.

In some examples, ICM 10 may use noise detection techniques, amplitude screening techniques, and/or confidence level techniques according to this disclosure. ICM 10 may use such techniques separately or in any combination. These techniques may be used to improve the accuracy of determination of QT or QTc intervals.

ICM 10 may incorporate noise detection techniques to detect noisy beats by detecting noisy QRS complexes and determining if the search window for the T-wave after the QRS is noisy. In some examples, ICM 10 may use noise detection techniques of this disclosure to determine if the R-wave is noisy and whether the ECG around the detected T-wave is noisy. In some examples, ICM 10 may analyze zero crossings and a rate of change (e.g., slope) of the cardiac signal to determine whether the cardiac signal is noisy. For example, if zero crossings have a high rate of change, that may be indicative of a noisy cardiac signal.

Figure 18:
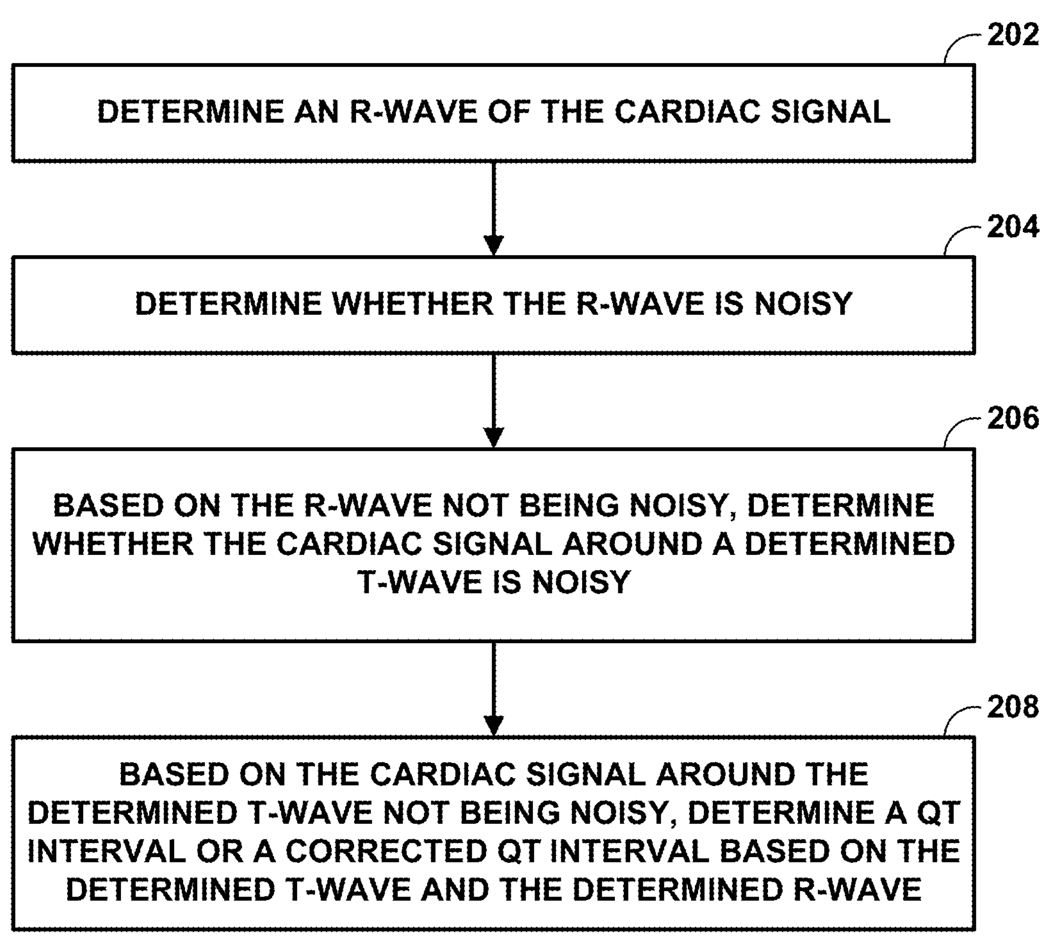
FIG. 18 is a flow diagram illustrating example noise determination techniques of this disclosure.

FIG. 18 is a flow diagram illustrating example noise determination techniques of this disclosure. Sensing circuitry 52 may determine an R-wave of the cardiac signal (202). For example, auto adjusting threshold process 104 and/or fixed threshold process 106 may determine a rectified signal from rectifier 102 has exceeded the auto adjusting threshold and/or the fixed threshold.

Processing circuitry 50 may determine whether the R-wave is noisy (204). For example, processing circuitry 50 may determine whether a rate of change of amplitude of a first plurality of samples of the cardiac signal around an R-wave peak is indicative of the R-wave being noisy. For example, processing circuitry 50 may determine an R-wave peak. In some examples, as part of determining the R-wave peak, processing circuitry 50 may determine a mean, median, or mode of amplitude of a plurality of second samples of the cardiac signal, a first sample of the second plurality of samples being before the determined R-wave and a last sample of the second plurality of samples being after the determined R-wave. For example, processing circuitry 50 may store, in storage device 84, a predetermined number of samples before a determined R-wave and a predetermined number of samples after the determined R-wave. In some examples, the predetermined number of samples before the determined R-wave and the predetermined number of samples after the determined R-wave are the same. In other examples, the predetermined number of samples before the determined R-wave and the predetermined number of samples after the determined R-wave are different. In some examples, the predetermined number of samples before the determined R-wave and the predetermined number of samples after the determined R-wave are 25 samples. However, the predetermined number of samples before the determined R-wave and the predetermined number of samples after the determined R-wave may be any number of samples. Processing circuitry 50 may determine a mean, median, or mode of amplitude of the plurality of second samples of the cardiac signal. A first sample of the second plurality of samples being before the determined R-wave and a last sample of the second plurality of samples being after the determined R-wave. For example, processing circuitry 50 may determine a mean of the second plurality of samples.

Processing circuitry 50 may determine a respective mean, median, or mode difference between the mean, median, or mode and each of the plurality of second samples. In other words, processing circuitry 50 may determine a difference between each of the samples of the plurality of second samples and the mean, median, or mode of the second plurality of samples. Processing circuitry 50 may determine an absolute value of each of the respective mean, median, or mode differences and determine the R-wave peak to be a highest absolute value of each of the respective mean, median, or mode differences. For example, processing circuitry 50 may determine the magnitude of the result of the subtraction regardless of the result of the subtractions being a positive or negative number. For example, if the result of the subtraction is −3, processing circuitry 50 may determine the absolute value of the result of the subtraction to be 3. If the result of the subtraction is 3, processing circuitry 50 may determine the absolute value of the result of the subtraction to be 3. For example, processing circuitry 50 may compare the absolute values for each sample and determine the sample with the highest absolute value of the group of samples to be the R-wave peak.

Processing circuitry 50 may store in storage device 84 a predetermined number of the first plurality of samples before and a predetermined number of the first plurality of samples after the determined R-wave peak. In some examples, the predetermined number of samples before and the predetermined number of samples after the determined R-wave peak are the same. In some examples, the predetermined number of samples before and the predetermined number of samples after the determined R-wave peak are different. In some examples, the predetermined number of samples before the determined R-wave peak is 15 and the predetermined number of samples after the determined R-wave peak is 16, however the predetermined number of samples before the determined R-wave peak and the predetermined number of samples after the determined R-wave peak may be any numbers.

Processing circuitry 50 may determine a plurality of first differences between the first plurality of samples of the cardiac signal. A first sample of the first plurality of samples being before the R-wave peak and a last sample of the first plurality of samples being after the R-wave peak. Each of the plurality of first differences may be a difference in amplitude of a respective sample of the first plurality of samples and a next sample of the first plurality of samples. For example, the first differences may include a difference in amplitude between a first sample and a second sample of the first plurality of samples, a difference in amplitude between the second sample and a third sample of the first plurality of samples, and so on. Thus, processing circuitry 50 may determine 31 first difference values in the example where there are 32 samples.

Processing circuitry 50 may determine a plurality of second differences between each of the plurality of first differences and a respective next difference of the plurality of first differences. For example, the plurality of second differences may include a difference between a first first-difference and a second first-difference, a difference between the second first-difference and a third first-difference, and so on. Thus, IMD 10 may determine 30 second difference values in the example where there are 31 first difference values.

Processing circuitry 50 may determine whether there is a sign change (e.g., from positive to negative, or from negative to positive) between each of the plurality of first differences and the respective next difference of the plurality of first differences. For example, processing circuitry 50 may determine that the first first-difference is positive and the second first-difference is negative. This would be a sign change. If the first first-difference is negative and the second first-difference is positive, this would also be a sign change. For each determined sign change, processing circuitry 50 may determine whether a magnitude of a corresponding second difference value is greater than a first predetermined noise threshold. For example, the first predetermined noise threshold may be 40. In some examples, the magnitude is an absolute value of the respective determined sign change. In some examples, there may be a positive first predetermined noise threshold and a negative first predetermined noise threshold and processing circuitry 50 may determine whether a magnitude of a respective corresponding second difference value is greater than the positive first predetermined noise threshold or lower than the negative first predetermined noise threshold.

Processing circuitry 50 may calculate a total number of sign changes in the first difference value with a corresponding second difference value greater than the positive first predetermined noise threshold or lower than the negative first predetermined noise threshold. For example, processing circuitry 50 may count the number of sign changes in the first difference value with a corresponding second difference value greater than the positive first predetermined noise threshold or lower than the negative first predetermined noise threshold. Processing circuitry 50 may determine whether the calculated total number is greater than a second predetermined noise threshold, for example, 8. For example, if the result of the counting is higher than the second predetermined noise threshold, processing circuitry 50 may consider the R-wave to be noisy. In such a case, the beat associated with the noisy R-wave may not be used to determine a QT or QTc interval. If the result of the counting is equal to or lower than the second predetermined noise threshold, processing circuitry 50 may consider the R-wave to not be noisy.

In some examples, processing circuitry 50 may use other techniques to determine whether the R-wave is noisy. For example, processing circuitry 50 may utilize a morphologic comparison to one or more templates. The one or more templates may be derived from recent data acquired from the patient or from longer-term historical data from the patient. In some examples, processing circuitry 50 may perform a root-mean-square error analysis to determine whether the R-wave is noisy.

Based on the R-wave not being noisy, processing circuitry 50 may determine whether the cardiac signal around a determined T-wave is noisy (206). For example, to check for noise around the determined T-wave, processing circuitry 50 may first map the T-wave location which may be determined as the sample with the highest slope from the rectified signal to the actual ECG. Since the rectified signal is shifted to the right when compared to the actual signal, the T-wave location in the actual signal may be, for example, the 18th sample before the T-wave location sample as determined by the algorithm in the rectified signal.

For example, processing circuitry 50 may store in storage device 84 a predetermined number of a third plurality of samples before and a predetermined number of the third plurality of samples after the determined T-wave actual location (e.g., the mapped T-wave). In some examples, the predetermined number of samples before and the predetermined number of samples after the determined T-wave actual location are the same. In some examples, the predetermined number of samples before and the predetermined number of samples after the determined T-wave actual location are different. In some examples, the predetermined number of samples before the determined T-wave actual location is 15 and the predetermined number of samples after the determined T-wave actual location is 16, however the predetermined number of samples before the determined T-wave actual location and the predetermined number of samples after the determined T-wave actual location may be any number.

For example, processing circuitry 50 may determine a plurality of third differences between a third plurality of samples of the cardiac signal, a first sample of the third plurality of samples being before the mapped T-wave and a last sample of the third plurality of samples being after the mapped T-wave. Each of the plurality of third differences may be a difference in amplitude of a respective sample of the third plurality of samples and a next sample of the third plurality of samples. For example, the plurality of third differences may include a difference in amplitude between a first sample and a second sample of the third plurality of samples, a difference in amplitude between the second sample and a third sample of the third plurality of samples, and so on.

Processing circuitry 50 may determine a plurality of fourth differences between each of the plurality of third differences and a respective next difference of the plurality of third differences. For example, the fourth differences may include a difference between a first third-difference and a second third-difference, a difference between the second third-difference and a third third-difference, and so on.

For example, by determining the plurality of third differences and the plurality of fourth differences, processing circuitry 50 may effectively high pass filter the mapped T-wave in the time domain with a lag which determined a desired frequency cut-off. The mapped T-wave may be slower than the R-wave, so the lag may be longer.

Processing circuitry 50 may determine whether there is a sign change (e.g., from positive to negative, or from negative to positive) between each of the plurality of third differences and the respective next difference of the plurality of third differences. For example, processing circuitry 50 may determine that the first third-difference is positive and the second third-difference is negative. This would be a sign change. If the first third-difference is negative and the second third-difference is positive, this would also be a sign change. For each determined sign change, processing circuitry 50 may determine whether a magnitude of a respective corresponding fourth difference value is greater than a positive third predetermined noise threshold or lower than a negative third predetermined noise threshold. For example, the positive third predetermined noise threshold may be 20 and the negative third predetermined threshold may be −20. In some examples, the magnitude is an absolute value of the respective magnitude of the corresponding fourth difference and processing circuitry 50 may determine whether a magnitude of a respective corresponding fourth difference value is greater than a third predetermined noise threshold, e.g., 20.

For example, processing circuitry 50 may calculate a total number of the corresponding fourth difference values having the magnitude greater than the positive third predetermined noise threshold or lower than the negative third predetermined noise threshold. In the examples where the magnitude is an absolute value, processing circuitry 50 may count the number of the corresponding fourth difference values having the magnitude greater than the positive third predetermined noise threshold. Processing circuitry 50 may determine whether the calculated total number is greater than a fourth predetermined noise threshold, for example, 5. For example, if the result of the counting is higher than the fourth predetermined noise threshold, processing circuitry 50 may consider the cardiac signal around the T-wave to be noisy. In such a case, the beat associated with the noisy ECG around the T-wave may not be used to determine a QT or QTc interval. If the result of the counting is equal to or lower than the predetermined number, IMD 10 may consider the ECG around the T-wave to not be noisy.

In some examples, processing circuitry 50 may use other techniques to determine whether the ECG around the T-wave is noisy. For example, processing circuitry 50 may utilize a morphologic comparison to one or more templates. The one or more templates may be derived from recent data acquired from the patient or from longer-term historical data from the patient. In some examples, processing circuitry 50 may perform a root-mean-square error analysis to determine whether the ECG around the T-wave is noisy.

Based on the cardiac signal around the determined T-wave not being noisy, processing circuitry 50 may determine a QT interval or a corrected QT interval based on the determined T-wave and the determined R-wave (208). For example, processing circuitry 50 may determine a time between an R-wave peak and the determined T-wave to be the QT interval. In other examples, processing circuitry 50 may determine the QT interval to be a number of samples between the R-wave peak and the determined T-wave. Processing circuitry 50 may also determine a QTc interval (150). For example, processing circuitry 50 may apply at least one of one of the Framingham formula, the Friderica formula or the Bazett formula or another formula or technique to the QT interval to determine the QTc interval. In some examples, processing circuitry 50 may consider a beat to be noisy and exclude that beat from a QT interval (or QTc) computation if either the beat's R-wave is noisy, or the cardiac signal around the beat's T-wave location is noisy. In some examples, if processing circuitry 50 determines a beat not to be noisy, processing circuitry 50 may employ feature (e.g., amplitude) screening techniques of this disclosure. Because processing circuitry 50 looks for noise only around the detected T-wave location, processing circuitry is not affected by noise in other parts of the cardiac signal in the current R-R segment.

In some examples, processing circuitry 50 may attempt to detect beats that are significantly different than other beats. In some examples, processing circuitry 50 may analyze morphology of beats and compare one or more features of the beats to determine a beat is significantly different than other beats. In some examples, processing circuitry 50 may map the determined T-wave as discussed above. In some examples, processing circuitry 50 may not map the determined T-wave. In some examples, processing circuitry 50 may determine whether at least one feature of the determined T-wave (whether mapped or not) is more than a predetermined difference threshold, such as 200, different than a mean, median, or mode of the at least one feature of a plurality of other T-waves. This may be performed to ensure that P-waves or noise are not being detected as a T-wave. In some examples, the at least one feature includes amplitude. In some examples, the determination of the QT interval is further based on the determined T-wave not being more than the predetermined difference threshold different than the mean, median, or mode of the at least one feature of the plurality of other T-waves, such as 8 other T-waves. For example, processing circuitry 50 may store a predetermined number of detected T-wave location amplitudes prior to the T-wave and a predetermined number of detected T-wave location amplitudes after the detected T-wave. In some examples, the predetermined number of detected T-wave location amplitudes prior to the T-wave and the predetermined number of detected T-wave location amplitudes after the detected T-wave are the same. In other examples, the predetermined number of detected T-wave location amplitudes prior to the T-wave and the predetermined number of detected T-wave location amplitudes after the detected T-wave are different. In some examples, the predetermined number of detected T-wave location amplitudes prior to the T-wave and the predetermined number of detected T-wave location amplitudes after the detected T-wave are each 4, but may be any number.

In some examples, as part of determining whether the determined T-wave is more than the predetermined difference threshold different than a plurality of other T-waves, processing circuitry 50 may determine whether a number of noisy beats of a predetermined number of beats is greater than the predetermined noisy beats threshold, a first beat of the predetermined number of beats being before the determined T-wave and a last beat of the predetermined number of beats being after the determined T-wave. In some examples, the predetermined noisy beats threshold may be a percentage of the predetermined number of beats, such as 50%. For example, processing circuitry 50 may determine whether the beats are noisy by employing the noise detection techniques discussed above with respect to each of the beats. If the number of noisy beats exceeds the predetermined noisy beats threshold, processing circuitry 50 may exclude the current beat from the QT interval analysis.

In some examples, if the number of noisy beats does not exceed the predetermined noisy beats threshold, processing circuitry 50 may determine a mean, median, or mode of amplitude of non-noisy beats of the predetermined number of beats. For example, IMD 10 may determine a median T-wave amplitude of the non-noisy beats of the predetermined number of detected T-wave location amplitudes prior to the T-wave and the predetermined number of detected T-wave location amplitudes after the detected T-wave. Processing circuitry 50 may also determine an absolute value of a difference between the mean, median, or mode of the amplitude of the non-noisy beats and the determined T-wave. Processing circuitry 50 may also determine whether the absolute value of the difference is greater than the predetermined difference threshold, e.g., 200. If the absolute value of the difference is greater than the predetermined difference threshold, IMD 10 may exclude the current beat from the QT interval (or QTc) computation.

IMD 10 implementing the amplitude screening techniques of this disclosure may exclude beats for which an R-wave is incorrectly detected as a T-wave. In some examples, IMD 10 implementing the amplitude screening techniques of this disclosure may exclude PVC beats. In some examples, IMD 10 implementing the amplitude screening techniques of this disclosure may exclude beats with a T-wave location that is significantly different from the other beats.

In some examples, processing circuitry 50 may determine a confidence level of the determined T-wave. In some examples, the confidence level is based on a degree of flatness of the cardiac signal around the determined T-wave. In some examples, the confidence metric may include confidence levels such as high, medium, or low. In some examples, processing circuitry 50 may determine the degree of flatness based on area under the curve between points selected on either side of the determined T-wave, amplitude of samples around the T-wave, slope analysis, or other techniques that would be indicative of a degree of flatness of the cardiac signal around the determined T-wave.

In some examples, as part of determining the degree of flatness, processing circuitry 50 may determine a mapped T-wave location as discussed above. In some examples, processing circuitry 50 may determine a maximum amplitude and a minimum amplitude of amplitudes of a fourth plurality of samples of the cardiac signal, a first sample of the fourth plurality of samples being before the mapped T-wave location and a last sample of the fourth plurality of samples being after the mapped T-wave location. For example, processing circuitry 50 may store in storage device 84 a predetermined number of samples before and a predetermined number of samples after a mapped T-wave. A T-wave may be mapped to the T-wave's actual location as mentioned above. In some examples, the predetermined number of samples prior to the T-wave and the predetermined number of samples after the detected T-wave are the same. In other examples, the predetermined number of samples prior to the T-wave and the predetermined number of samples after the detected T-wave are different. In some examples, the predetermined number of samples prior to the T-wave and the predetermined number of samples after the detected T-wave are each 20, but may be any number.

In other examples, processing circuitry 50 may determine a mapped T-wave location by comparing different lag differences or by a morphologic comparison to one or more templates. The one or more templates may be derived from recent data acquired from the patient or from longer-term historical data from the patient.

Processing circuitry 50 may determine whether an absolute value of a difference between the maximum amplitude and the minimum amplitude is greater than or equal to a first predetermined confidence threshold, whether the absolute value of the difference is less than or equal to a second predetermined confidence threshold, or whether the absolute value of the difference is between the first predetermined confidence threshold and the second predetermined confidence threshold. For example, processing circuitry 50 may determine a maximum amplitude among the stored samples and a minimum amplitude among the stored fourth plurality of samples. For example, processing circuitry 50 may determine the amplitude of the sample with the highest amplitude to be the maximum amplitude and the amplitude of the sample with the lowest amplitude to be the minimum amplitude.

Processing circuitry 50 may determine a difference between the maximum amplitude and minimum amplitude and may determine the absolute value of that difference.

Processing circuitry 50 may compare the absolute value of the difference to an upper threshold and/or a lower threshold. In some examples, the upper threshold is 35 and the lower threshold is 25. If the absolute value of the difference is greater than or equal to the upper threshold, processing circuitry may assign a high confidence level to that beat. If the absolute value of the difference is lesser than or equal to the lower threshold, processing circuitry 50 may assign a low confidence level to the beat. If the absolute value of the difference is between the upper threshold and the lower threshold, processing circuitry 50 may assign a medium confidence level to the beat. In some examples, processing circuitry 50 may exclude beats with a low confidence metric from QT interval (or QTc) analysis.

In some examples, processing circuitry 50 of ICM 10 may determine a mean, median, mode, standard deviation or any other trend of determined QT intervals or QTc intervals over time. ICM 10 may communicate the mean, median, mode, standard deviation or any other trend of the determined QTc intervals to external device 12. In some examples, ICM 10 may determine a time or count of which QT intervals or QTc intervals are longer than a predetermined threshold. This predetermined threshold may be in the order of 500 ms, for example, as QT intervals greater than 500 ms may correlate to a higher risk of torsades de pointes. In some examples, ICM 10 may determine a time or count of QT intervals or QTc intervals that change greater than a threshold. For example, ICM 10 may determine a time or count of QT interval or QTc intervals that change greater than 30 ms or 40 ms or some other threshold (which may even be patient specific) within a specific time period.

Figure 19A:
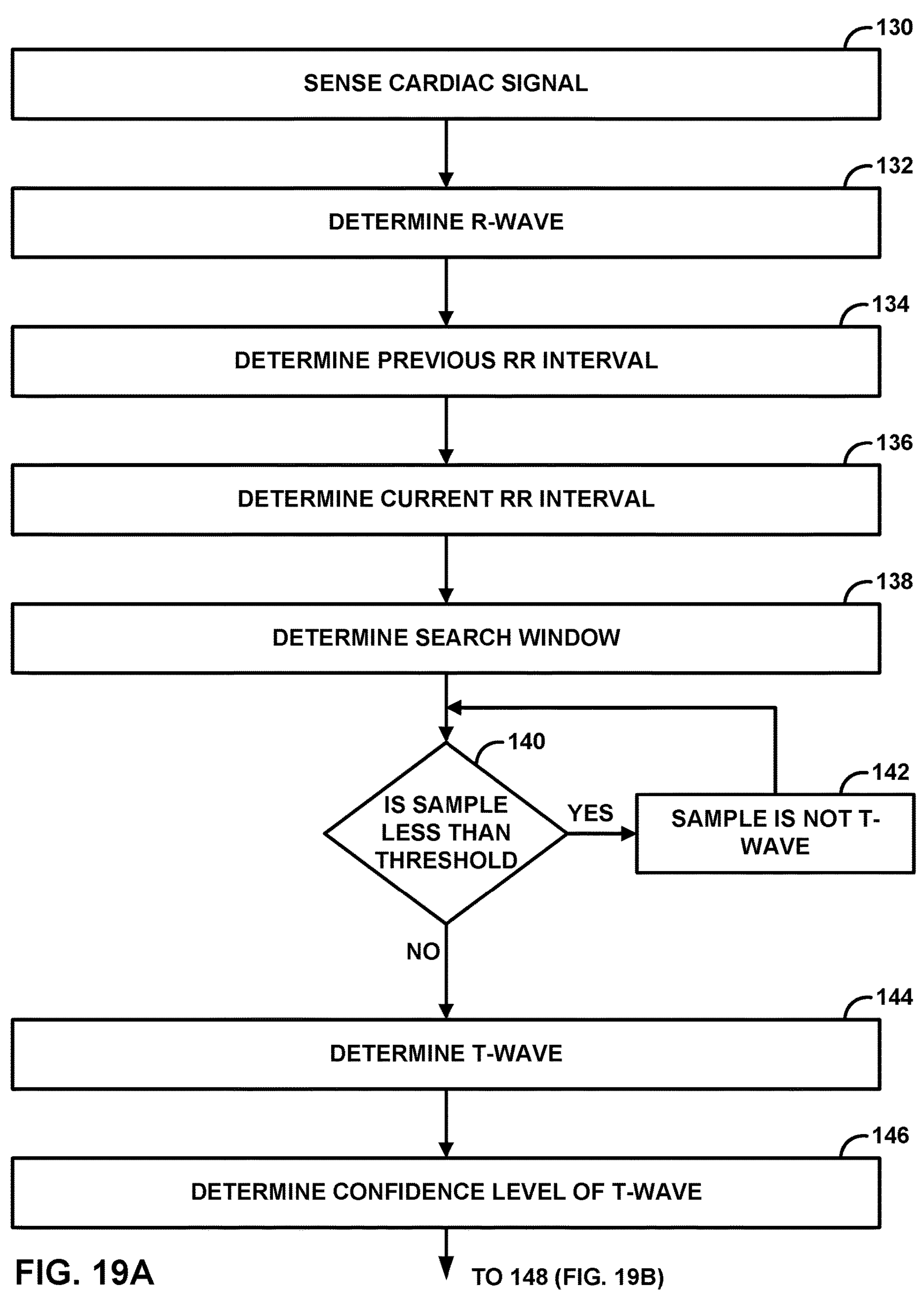
FIGS. 19A-B are flow diagrams illustrating example techniques of this disclosure.

FIG. 19A is a flow diagram illustrating example techniques of this disclosure. Sensing circuitry 52 of ICM 10 may sense a cardiac signal (130). In some examples, sensing circuitry 52 may apply one or more band-pass filters (e.g., band-pass filter 100) or rectifiers (e.g., rectifier 102) to a cardiac signal. In some examples, sensing circuitry 52 may use a primary sensing channel 108 and a secondary sensing channel 110 to sense the cardiac signal.

Sensing circuitry 52 may determine an R-wave of the cardiac signal (132). For example, auto adjusting threshold process 104 and/or fixed threshold process 106 may determine a rectified signal from rectifier 102 has exceeded the auto adjusting threshold and/or the fixed threshold. Processing circuitry 50 of ICM 10 may determine a previous RR interval (134). For example, to accurately determine the previous RR interval, processing circuitry 50 may determine a peak R value in a two consecutive sensed R-waves (e.g., peak_current_sample and peak_previous_sample). Processing circuitry 50 may determine the previous RR interval to be the time between the two consecutive peak R values, peak_current_sample and peak_previous_sample. In some examples, processing circuitry 50 may take a first predetermined number of samples before the sensed R-wave and a second predetermined number of samples after the sensed R-wave at a predetermined frequency and determine the sample with the maximum amplitude is the R-wave peak sample.

Processing circuitry 50 of ICM 10 may also determine a current RR interval (136). For example, to accurately determine the current RR interval, processing circuitry 50 may determine a peak R value in for a next sensed R-wave (e.g., peak_next_sample). Processing circuitry 50 may determine peak_next_sample in the same or similar manner to that used to determine peak_current_sample and peak_previous_sample. Processing circuitry 50 may determine the current RR interval to be the time between the two consecutive peak R values, peak_next_sample and peak_current_sample.

Processing circuitry 50 may then determine a search window to search for a T-wave based on one or more of the current RR interval or the previous RR interval. Processing circuitry 50 may determine the search window to start at a number of samples after an R-wave peak and end a different number of samples after the R-wave peak. These numbers of samples may be based on the length of the current RR interval or the previous RR interval. In some examples, the numbers of samples may be stored in storage device 56, such as in a look-up table. In some examples, the numbers of samples may be those set forth above in Tables 1 and 2.

In some examples, processing circuitry 50 may utilize a threshold to assist in determining a T-wave. In other examples, processing circuitry may not utilize a threshold. For example, processing circuitry 50 may determine whether an amplitude of a sample is less than a threshold (or in some instances less than or equal to) (140). If the amplitude of a sample is less than the threshold (or in some instances less than or equal to) (the "YES" path in FIG. 18A), processing circuitry 50 may determine the sample is not a T-wave (142). Processing circuitry 50 may then examine the next sample. If the amplitude of a sample is equal to or greater than the threshold (or in some instances greater than), processing circuitry 50 may keep that sample as a candidate for as T-wave (the "NO" path of FIG. 18A).

Processing circuitry 50 may determine a T-wave of the cardiac signal in the search window (144). For example, processing circuitry 50 may determine the highest amplitude sample in the search window to be the T-wave. In other examples, processing circuitry 50 may take a predetermined number of samples around a given sample and determine a median, mean or mode and determine the T-wave to be the maximum amplitude median, mean or mode in the search window.

In some examples, processing circuitry 50 may determine a confidence level for the T-wave (146). In some examples, processing circuitry 50 may not determine a confidence level for the T-wave. For example, processing circuitry 50 may determine a confidence level based on one or more of a predetermined number of previous T-wave amplitudes or QT intervals. For example, if the amplitude of a detected T-wave is too low compared to previous T-waves or if the QT interval is very different from the previous 12 QT intervals, then ICM 10 may give the detected T-wave a low confidence level.

Figure 19B:
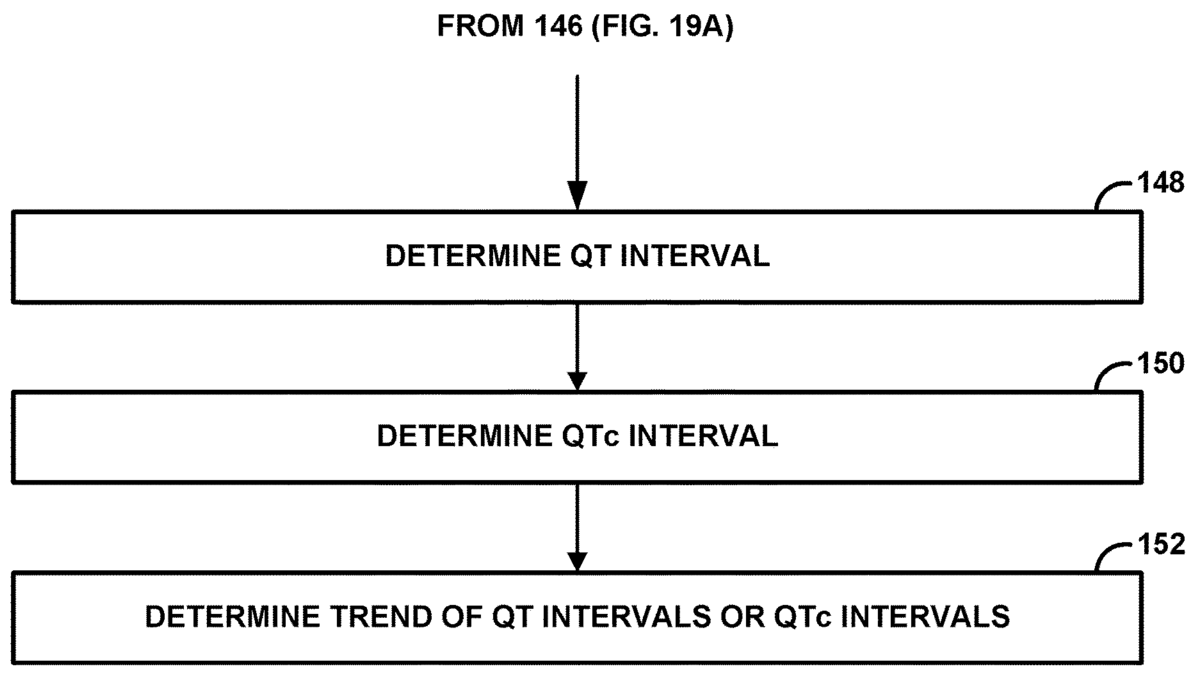

FIG. 19B is a continuation of FIG. 19A. Processing circuitry 50 may determine a QT interval based on the determined T-wave and the determined R-wave (148). For example, processing circuitry 50 may determine a time between an R-wave peak and the determined T-wave to be the QT interval. In other examples, processing circuitry 50 may determine the QT interval to be a number of samples between the R-wave peak and the determined T-wave. Processing circuitry 50 may also determine a QTc interval (150). For example, processing circuitry 50 may apply at least one of one of the Framingham formula, the Friderica formula or the Bazett formula or another formula or technique to the QT interval to determine the QTc interval.

Processing circuitry 50 may determine a trend of QT intervals or QTc intervals over time (152). For example, processing circuitry 50 may determine a mean, median, mode, standard deviation or any other trend of determined QT intervals or QTc intervals over time.

Figure 20:
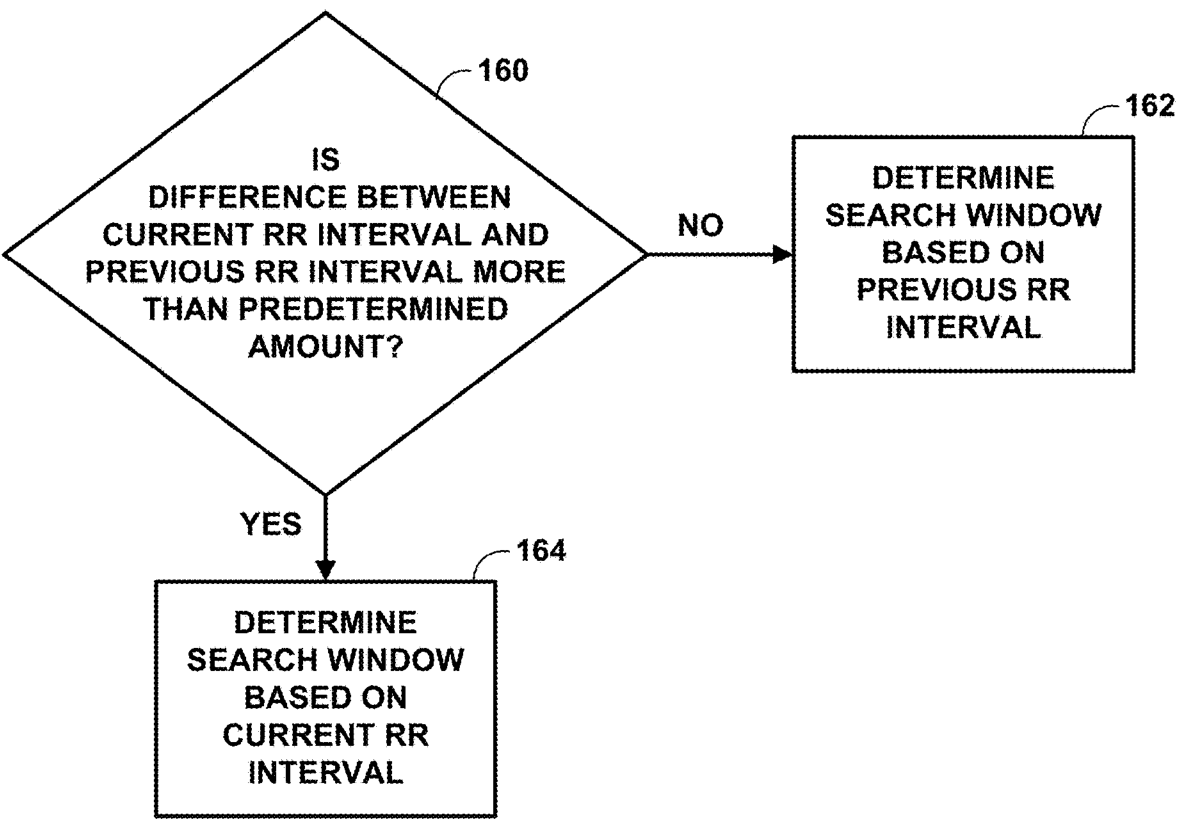
FIG. 20 is a flow diagram illustrating an example technique of this disclosure.

FIG. 20 is a flow diagram depicting one example of how processing circuitry 50 may determine whether to base the search window on the previous RR interval or the current RR interval, e.g., as part of determining the search window (138 of FIG. 19A). In the example of FIG. 20, processing circuitry 50 may determine whether the difference between the current RR interval and the previous RR interval is more than a predetermined amount (160). For example, processing circuitry 50 may determine whether the difference between the current RR interval and the previous RR interval is more than a predetermined time period. In another example, processing circuitry 50 may determine whether the difference between the current RR interval and the previous RR interval is more than a predetermined number of samples larger. In some examples, if the difference between the current RR interval and the previous RR interval is not more than a predetermined amount (the "NO" path in FIG. 20), processing circuitry 50 may determine the search window based on the previous RR interval (162). If the difference between the current RR interval and the previous RR interval is more than a predetermined amount (the "YES" path in FIG. 20), processing circuitry 50 may determine the search window based on the current RR interval (164). In some examples, the predetermined amount may be 500 ms. In some examples, the predetermined amount may be 128 samples at 256 Hz.

Figure 21:
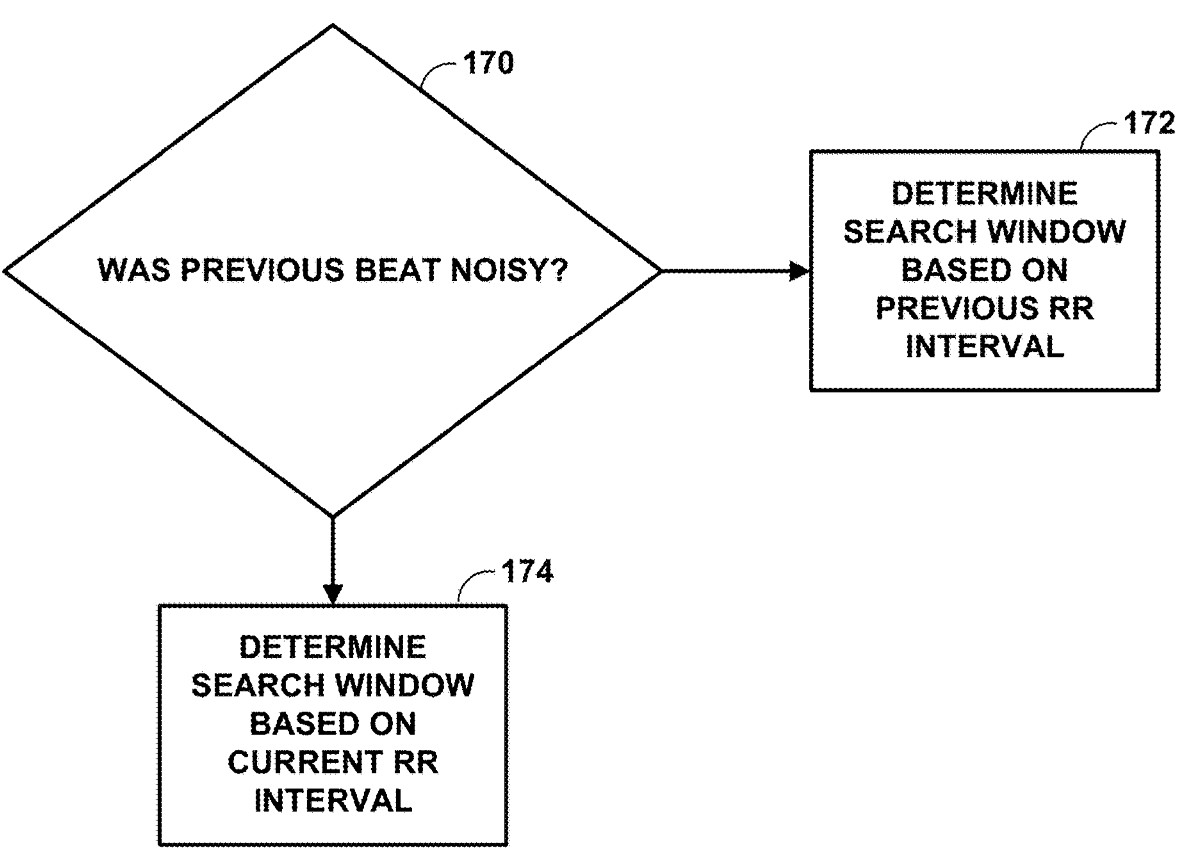
FIG. 21 is a flow diagram illustrating an example technique of this disclosure.

FIG. 21 is a flow diagram depicting another example of how processing circuitry 50 may determine whether to base the search window on the previous RR interval or the current RR interval, e.g., as part of determining the search window (138 of FIG. 19A). In the example of FIG. 21, processing circuitry may determine if a previous beat was noisy (170). For example, ICM 10 may be configured to detect a noisy beat. For example, processing circuitry 50 may determine whether a beat is noisy by determining whether the current R wave is noisy or the ECG segment between the current R wave and the next R wave is noisy or both. For example, processing circuitry may determine whether the current R wave is noisy by defining a window of a few samples before the R wave peak and a few samples after the R wave peak. Processing circuitry 50 may determine a noise count by counting the number of samples in the window where there is a sign change of greater than a first threshold (e.g., 50) or a sign change of less than a second threshold (e.g., −50). If this noise count is greater than or equal to a threshold (e.g., 5) then processing circuitry 50 may determine the beat is noisy. Processing circuitry 50 may determine whether the segment between the current R wave and the next R wave is noisy in a similar manner. In this case, processor circuitry 50 may define a window starting from a few samples after the current R wave and ending a few samples before the next R wave. Processing circuitry 50 may determine a noise count in a similar manner although the thresholds may be different. If the noise count, is greater than or equal to another threshold (e.g., 5 or some other count), then processing circuitry may determine that the beat is noisy.

If processing circuitry 50 determines that the previous beat was not noisy (the "NO" path in FIG. 21), processing circuitry 50 may determine the search window based on the previous RR interval (172). If processing circuitry 50 determines that the previous beat was noisy (the "YES" path in FIG. 21), processing circuitry 50 may determine the search window based on the current interval.

While the techniques herein are described as being performed by various elements, such as sensing circuitry 52 and processing circuitry 50, in some examples, other elements or a combination of elements may perform the techniques. For example, sensing circuitry 52 may perform techniques described as being performed by processing circuitry 50, processing circuitry 50 may perform techniques described as being performed by sensing circuitry 52, or a combination of sensing circuitry 52 and processing circuitry 50 may perform techniques described as being performed by either.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a non-transitory computer-readable storage medium such as RAM, ROM, NVRAM, EEPROM, FLASH memory, magnetic media, optical media, or the like. The instructions may be executed to support one or more aspects of the functionality described in this disclosure.

This disclosure includes the following non-limiting examples.

Example 1. A device comprising: one or more electrodes; sensing circuitry configured to sense a cardiac signal via the one or more electrodes; and processing circuitry configured to: determine an R-wave of the cardiac signal; determine whether the R-wave is noisy; based on the R-wave not being noisy, determine whether the cardiac signal around a determined T-wave is noisy; and based on the cardiac signal around the determined T-wave not being noisy, determine a QT interval or a corrected QT interval based on the determined T-wave and the determined R-wave.

Example 2. The device of example 1, wherein as part of determining whether the R-wave is noisy, the processing circuitry is configured to: determine whether a rate of change of amplitude of a plurality of samples of the cardiac signal around an R-wave peak is indicative of the R-wave being noisy.

Example 3. The device of example 2, wherein as part of determining whether a rate of change of amplitude of a plurality of samples of the cardiac signal around an R-wave peak is indicative of the R-wave being noisy, the processing circuitry is configured to: determine a peak of the R-wave; determine a plurality of first differences between a first plurality of samples of the cardiac signal, a first sample of the first plurality of samples being before the R-wave peak and a last sample of the first plurality of samples being after the R-wave peak, each of the plurality of first differences being a difference in amplitude of a respective sample of the first plurality of samples and a next sample of the first plurality of samples; determine a plurality of second differences between each of the plurality of first differences and a respective next difference of the plurality of first differences; determine whether there is a sign change between each of the plurality of first differences and the respective next difference of the plurality of first differences; for each determined sign change, determine whether a magnitude of a respective corresponding second difference value is greater than a first positive predetermined noise threshold or lower than a first negative predetermined noise threshold; calculate a total number of the corresponding second difference values having the magnitude greater than the positive first predetermined noise threshold or lower than the negative first predetermined noise threshold; and determine whether the calculated total number is greater than a second predetermined noise threshold.

Example 4. The device of example 3, wherein as part of determining the R-wave peak, the processing circuitry is configured to: determine a mean, median, or mode of amplitude of a plurality of second samples of the cardiac signal, a first sample of the second plurality of samples being before the determined R-wave and a last sample of the second plurality of samples being after the determined R-wave; determine a respective mean, median, or mode difference between the mean, median, or mode and each of the plurality of second samples; determine an absolute value of each of the respective mean, median, or mode differences; and determine the R-wave peak to be a highest absolute value of each of the respective mean, median, or mode differences.

Example 5. The device of any combination of examples 1-4, wherein as part of determining whether the cardiac signal around the determined T-wave is noisy, the processing circuitry is configured to: determine a plurality of third differences between a third plurality of samples of the cardiac signal, a first sample of the third plurality of samples being before the determined T-wave and a last sample of the third plurality of samples being after the determined T-wave, each of the plurality of third differences being a difference in amplitude of a respective sample of the third plurality of samples and a next sample of the third plurality of samples; determine a plurality of fourth differences between each of the plurality of third differences and a respective next difference of the plurality of third differences; determine whether there is a sign change between each of the plurality of third differences and the respective next difference of the plurality of third differences; for each determined sign change, determine whether a magnitude of a respective corresponding fourth difference value is greater than a positive third predetermined noise threshold or lower than a negative third predetermined noise threshold; calculate a total number of the corresponding second difference values having the magnitude greater than the positive third predetermined noise threshold or lower than the negative third predetermined noise threshold; and determine whether the calculated total number is greater than a fourth predetermined noise threshold.

Example 6. The device of any combination of examples 1-5, wherein the processing circuitry is further configured to: determine whether at least one feature of the determined T-wave is more than a predetermined difference threshold different than a mean, median, or mode of the at least one feature of a plurality of other T-waves, wherein the determination of the QT interval is further based on the determined T-wave not being more than the predetermined difference threshold different than the mean, median, or mode of the at least one feature of the plurality of other T-waves.

Example 7. The device of example 6, wherein as part of determining whether the determined T-wave is more than the predetermined difference threshold different than a plurality of other T-waves, the processing circuitry is configured to: determine whether a number of noisy beats of a predetermined number of beats is greater than a predetermined noisy beats threshold, a first beat of the predetermined number of beats being before the determined T-wave and a last beat of the predetermined number of beats being after the determined T-wave.

Example 8. The device of example 7, wherein as part of determining whether the determined T-wave is more than the predetermined difference threshold different than a plurality of other T-waves, the processing circuitry is configured to: determine a mean, median, or mode of amplitude of non-noisy beats of the predetermined number of beats; determine an absolute value of a difference between the mean, median, or mode of the amplitude of the non-noisy beats and the determined T-wave; and determine whether the absolute value of the difference is greater than the predetermined difference threshold.

Example 9. The device of any combination of examples 1-8, wherein the processing circuitry is further configured to: determine a confidence level of the determined T-wave.

Example 10. The device of example 9, wherein the confidence level is based on a degree of flatness of the cardiac signal around the determined T-wave.

Example 11. The device of example 10, wherein the processing circuitry is configured to determine the degree of flatness, wherein as part of determining the degree of flatness, the processing circuitry is configured to: determine a mapped T-wave location; determine a maximum amplitude and a minimum amplitude of amplitudes of a plurality of samples of the cardiac signal, a first sample of the plurality of samples being before the mapped T-wave location and a last sample of the plurality of samples being after the mapped T-wave location; and determine whether an absolute value of a difference between the maximum amplitude and the minimum amplitude is greater than or equal to a first predetermined confidence threshold, whether the absolute value of the difference is less than or equal to a second predetermined confidence threshold, or whether the absolute value of the difference is between the first predetermined confidence threshold and the second predetermined confidence threshold.

Example 12. A method comprising: determining, by processing circuitry, an R-wave of a cardiac signal; determining, by the processing circuitry, whether the R-wave is noisy; based on the R-wave not being noisy, determining, by the processing circuitry, whether the cardiac signal around a determined T-wave is noisy; and based on the cardiac signal around the determined T-wave not being noisy, determining, by the processing circuitry, a QT interval or a corrected QT interval based on the determined T-wave and the determined R-wave.

Example 13. The method of example 12, wherein determining whether the R-wave is noisy comprises: determining, by the processing circuitry, whether a rate of change of amplitude of a plurality of samples of the cardiac signal around an R-wave peak is indicative of the R-wave being noisy.

Example 14. The method of example 13, wherein determining whether a rate of change of amplitude of a plurality of samples of the cardiac signal around an R-wave peak is indicative of the R-wave being noisy comprises: determining, by the processing circuitry, a peak of the R-wave; determining, by the processing circuitry, a plurality of first differences between a first plurality of samples of the cardiac signal, a first sample of the first plurality of samples being before the R-wave peak and a last sample of the first plurality of samples being after the R-wave peak, each of the plurality of first differences being a difference in amplitude of a respective sample of the first plurality of samples and a next sample of the first plurality of samples; determining, by the processing circuitry, a plurality of second differences between each of the plurality of first differences and a respective next difference of the plurality of first differences; determining, by the processing circuitry, whether there is a sign change between each of the plurality of first differences and the respective next difference of the plurality of first differences; for each determined sign change, determining, by the processing circuitry, whether a magnitude of a respective corresponding second difference value is greater than a first positive predetermined noise threshold or lower than a first negative predetermined noise threshold; calculating, by the processing circuitry, a total number of the corresponding second difference values having the magnitude greater than the positive first predetermined noise threshold or lower than the negative first predetermined noise threshold; and determining, by the processing circuitry, whether the calculated total number is greater than a second predetermined noise threshold.

Example 15. The method of example 14, wherein determining the R-wave peak comprises: determining, by the processing circuitry, a mean, median, or mode of amplitude of a plurality of second samples of the cardiac signal, a first sample of the second plurality of samples being before the determined R-wave and a last sample of the second plurality of samples being after the determined R-wave; determining, by the processing circuitry, a respective mean, median, or mode difference between the mean, median, or mode and each of the plurality of second samples; determining, by the processing circuitry, an absolute value of each of the respective mean, median, or mode differences; and determining, by the processing circuitry, the R-wave peak to be a highest absolute value of each of the respective mean, median, or mode differences.

Example 16. The method of any combination of examples 12-15, wherein determining whether the ECG around the determined T-wave is noisy comprises: determining, by the processing circuitry, a plurality of third differences between a third plurality of samples of the cardiac signal, a first sample of the third plurality of samples being before the determined T-wave and a last sample of the third plurality of samples being after the determined T-wave, each of the plurality of third differences being a difference in amplitude of a respective sample of the third plurality of samples and a next sample of the third plurality of samples; determining, by the processing circuitry, a plurality of fourth differences between each of the plurality of third differences and a respective next difference of the plurality of third differences; determining, by the processing circuitry, whether there is a sign change between each of the plurality of third differences and the respective next difference of the plurality of third differences; for each determined sign change, determining, by the processing circuitry, whether a magnitude of a respective corresponding fourth difference value is greater than a positive third predetermined noise threshold or lower than a negative third predetermined noise threshold; calculating, by the processing circuitry, a total number of the corresponding second difference values having the magnitude greater than the positive third predetermined noise threshold or lower than the negative third predetermined noise threshold; and determining, by the processing circuitry, whether the calculated total number is greater than a fourth predetermined noise threshold.

Example 17. The method of any combination of examples 12-16, further comprising: determining, by the processing circuitry, whether at least one feature of the determined T-wave is more than a predetermined difference threshold different than a mean, median, or mode of the at least one feature of a plurality of other T-waves, wherein the determination of the QT interval is further based on the determined T-wave not being more than the predetermined difference threshold different than the mean, median, or mode of the at least one feature of the plurality of other T-waves.

Example 18. The method of example 17, wherein determining whether the determined T-wave is more than the predetermined difference threshold different than a plurality of other T-waves comprises: determining, by the processing circuitry, whether a number of noisy beats of a predetermined number of beats is greater than a predetermined noisy beats threshold, a first beat of the predetermined number of beats being before the determined T-wave and a last beat of the predetermined number of beats being after the determined T-wave.

Example 19. The method of example 18, wherein determining whether the determined T-wave is more than the predetermined difference threshold different than a plurality of other T-waves comprises: determining, by the processing circuitry, a mean, median, or mode of amplitude of non-noisy beats of the predetermined number of beats; and determining, by the processing circuitry, an absolute value of a difference between the mean, median, or mode of the amplitude of the non-noisy beats and the determined T-wave; and determining, by the processing circuitry, whether the absolute value of the difference is greater than the predetermined difference threshold.

Example 20. The method of any combination of examples 12-19, further comprising: determining, by the processing circuitry, a confidence level of the determined T-wave.

Example 21. The method of example 20, wherein the confidence level is based on a degree of flatness of the cardiac signal around the determined T-wave.

Example 22. The method of example 21, further comprising: determining, by the processing circuitry, the degree of flatness, wherein determining the degree of flatness comprises: determining, by the processing circuitry, a mapped T-wave location; determining, by the processing circuitry, a maximum amplitude and a minimum amplitude of amplitudes of a fourth plurality of samples of the cardiac signal, a first sample of the fourth plurality of samples being before the mapped T-wave location and a last sample of the fourth plurality of samples being after the mapped T-wave location; and determining, by the processing circuitry, whether an absolute value of a difference between the maximum amplitude and the minimum amplitude is greater than or equal to a first predetermined confidence threshold, whether the absolute value of the difference is less than or equal to a second predetermined confidence threshold, or whether the absolute value of the difference is between the first predetermined confidence threshold and the second predetermined confidence threshold.

Example 23. A non-transitory, computer-readable storage medium storing a set of instructions that, when executed, cause a system to: determine an R-wave of the cardiac signal; determine whether the R-wave is noisy; based on the R-wave not being noisy, determine whether the cardiac signal around a determined T-wave is noisy; and based on the cardiac signal around the determined T-wave not being noisy, determine a QT interval or a corrected QT interval based on the determined T-wave and the determined R-wave.

Various examples have been described. These and other examples are within the scope of the following claims.

What is claimed is:

1. An implantable medical device comprising:

a housing configured to be implanted within a patient;

a plurality of electrodes;

sensing circuitry disposed within the housing configured to sense a cardiac signal based on electrical activity of a heart of the patient via the plurality of electrodes; and processing circuitry configured to:

determine an R-wave of the cardiac signal;

determine one or more RR intervals, wherein the one or more RR intervals comprise at least one of a previous RR interval associated with the determined R-wave or a current RR interval associated with the determined R-wave;

determine a T-wave of the cardiac signal based on filtering at least a portion of the one or more RR intervals of the cardiac signal;

determine at least one of a QT interval or a QTc interval based on the determined T-wave and the determined R-wave; and at least one of predict or detect an abnormal cardiac rhythm based at least in part on the at least one of the QT interval or the corrected QT interval.

2. The implantable medical device of claim 1, wherein as part of determining the R-wave, the processing circuitry is configured to filter at least a portion of the cardiac signal.

3. The implantable medical device of claim 1, wherein as part of determining the R-wave the processing circuitry is configured to apply a first set of one or more filters to the cardiac signal, and wherein as part of determining the T-wave the processing circuitry is configured to apply a second set of one or more filters to the at least a portion of the one or more RR intervals, the second set of one or more filters comprising at least one filter different than each filter of the first set of filters.

4. The implantable medical device of claim 1, wherein as part of determining the T-wave, the processing circuitry is configured to weight amplitudes of samples more heavily that are more likely to be located where the T-wave is located in the at least a portion of the one or more RR intervals than samples that are less likely to be located where the T-wave is located based on previous QT intervals or previous QTc intervals.

5. The implantable medical device of claim 1, wherein as part of determining the T-wave, the processing circuitry is configured to determine a maximum median value of samples in the at least a portion of the one or more RR intervals.

6. The implantable medical device of claim 1, wherein the processing circuitry is further configured to determine a confidence level of the T-wave based on one or more of a predetermined number of previous T-wave amplitudes, QT intervals, or QTc intervals.

7. The implantable medical device of claim 1, wherein as part of the at least one of predict or detect an abnormal cardiac rhythm the processing circuitry is further configured to determine a time or a count of which QT intervals or QTc intervals are longer than a predetermined threshold.

8. The implantable medical device of claim 1, wherein the processing circuitry is further configured to:

determine whether at least a portion of the cardiac signal is noisy; and based on the at least a portion of the cardiac signal not being noisy, determine the at least one of the QT interval or the QTc interval.

9. The implantable medical device of claim 8, wherein the at least a portion of the cardiac signal comprises the R-wave, and wherein as part of determining whether the at least a portion of the cardiac signal is noisy, the processing circuitry is configured to:

determine an R-wave peak of the R-wave;

determine a plurality of first differences between a first plurality of samples of the cardiac signal, a first sample of the first plurality of samples being before the R-wave peak and a last sample of the first plurality of samples being after the R-wave peak, each of the plurality of first differences being a difference in amplitude of a respective sample of the first plurality of samples and a next sample of the first plurality of samples;

determine a plurality of second differences between each of the plurality of first differences and a respective next difference of the plurality of first differences;

determine whether there is a sign change between each of the plurality of first differences and the respective next difference of the plurality of first differences;

for each determined sign change, determine whether a magnitude of a respective corresponding second difference value is greater than a first positive predetermined noise threshold or lower than a first negative predetermined noise threshold;

calculate a total number of the corresponding second difference values having the magnitude greater than the positive first predetermined noise threshold or lower than the negative first predetermined noise threshold; and determine whether the calculated total number is greater than a second predetermined noise threshold.

10. The implantable medical device of claim 8, wherein the at least a portion of the cardiac signal comprises an area around the T-wave, and wherein as part of determining whether the at least a portion of the cardiac signal is noisy, the processing circuitry is configured to:

determine a plurality of third differences between a third plurality of samples of the cardiac signal, a first sample of the third plurality of samples being before a mapped T-wave and a last sample of the third plurality of samples being after the mapped T-wave, each of the plurality of third differences being a difference in amplitude of a respective sample of the third plurality of samples and a next sample of the third plurality of samples;

determine a plurality of fourth differences between each of the plurality of third differences and a respective next difference of the plurality of third differences;

determine whether there is a sign change between each of the plurality of third differences and the respective next difference of the plurality of third differences;

for each determined sign change, determine whether a magnitude of a respective corresponding fourth difference value is greater than a positive third predetermined noise threshold or lower than a negative third predetermined noise threshold;

calculate a total number of the corresponding second difference values having the magnitude greater than the positive third predetermined noise threshold or lower than the negative third predetermined noise threshold; and determine whether the calculated total number is greater than a fourth predetermined noise threshold.

11. A computing device comprising:

communication circuitry configured to receive a cardiac signal from an implantable medical device having a housing, a plurality of electrodes, and sensing circuitry disposed within the housing configured to sense the cardiac signal based on electrical activity of a heart of a patient via the plurality of electrodes; and processing circuitry configured to:

determine an R-wave of the cardiac signal;

determine one or more RR intervals, wherein the one or more RR intervals comprise at least one of a previous RR interval associated with the determined R-wave or a current RR interval associated with the determined R-wave;

determine a T-wave of the cardiac signal based on filtering at least a portion of the one or more RR intervals of the cardiac signal;

determine at least one of a QT interval or a QTc interval based on the determined T-wave and the determined R-wave; and at least one of predict or detect an abnormal cardiac rhythm based at least in part on the at least one of the QT interval or the corrected QT interval.

12. The computing device of claim 11, wherein as part of determining the R-wave, the processing circuitry is configured to filter at least a portion of the cardiac signal.

13. The computing device of claim 11, wherein as part of determining the R-wave the processing circuitry is configured to apply a first set of one or more filters to the cardiac signal, and wherein as part of determining the T-wave the processing circuitry is configured to apply a second set of one or more filters to the at least a portion of the one or more RR intervals, the second set of one or more filters comprising at least one filter different than each filter of the first set of filters.

14. The computing device of claim 11, wherein as part of determining the T-wave, the processing circuitry is configured to weight amplitudes of samples more heavily that are more likely to be located where the T-wave is located in the at least a portion of the one or more RR intervals than samples that are less likely to be located where the T-wave is located based on previous QT intervals or previous QTc intervals.

15. The computing device of claim 11, wherein as part of determining the T-wave, the processing circuitry is configured to determine a maximum median value of samples in the at least a portion of the at least a portion of the one or more RR intervals.

16. The computing device of claim 11, wherein the processing circuitry is further configured to determine a confidence level of the T-wave based on one or more of a predetermined number of previous T-wave amplitudes, QT intervals, or QTc intervals.

17. The computing device of claim 11, wherein as part of the at least one of predict or detect an abnormal cardiac rhythm the processing circuitry is further configured to determine a time or a count of which QT intervals or QTc intervals are longer than a predetermined threshold.

18. The computing device of claim 11, wherein the processing circuitry is further configured to:

determine whether at least a portion of the cardiac signal is noisy; and based on the at least a portion of the cardiac signal not being noisy, determine the at least one of the QT interval or the QTc interval.

19. The computing device of claim 18, wherein the at least a portion of the cardiac signal comprises the R-wave, and wherein as part of determining whether the at least a portion of the cardiac signal is noisy, the processing circuitry is configured to:

determine an R-wave peak of the R-wave;

determine a plurality of first differences between a first plurality of samples of the cardiac signal, a first sample of the first plurality of samples being before the R-wave peak and a last sample of the first plurality of samples being after the R-wave peak, each of the plurality of first differences being a difference in amplitude of a respective sample of the first plurality of samples and a next sample of the first plurality of samples;

determine a plurality of second differences between each of the plurality of first differences and a respective next difference of the plurality of first differences;

determine whether there is a sign change between each of the plurality of first differences and the respective next difference of the plurality of first differences;

for each determined sign change, determine whether a magnitude of a respective corresponding second difference value is greater than a first positive predetermined noise threshold or lower than a first negative predetermined noise threshold;

calculate a total number of the corresponding second difference values having the magnitude greater than the positive first predetermined noise threshold or lower than the negative first predetermined noise threshold; and determine whether the calculated total number is greater than a second predetermined noise threshold.

20. The computing device of claim 18, wherein the at least a portion of the cardiac signal comprises an area around the T-wave, and wherein as part of determining whether the at least a portion of the cardiac signal is noisy, the processing circuitry is configured to:

determine a plurality of third differences between a third plurality of samples of the cardiac signal, a first sample of the third plurality of samples being before a mapped T-wave and a last sample of the third plurality of samples being after the mapped T-wave, each of the plurality of third differences being a difference in amplitude of a respective sample of the third plurality of samples and a next sample of the third plurality of samples;

determine a plurality of fourth differences between each of the plurality of third differences and a respective next difference of the plurality of third differences;

determine whether there is a sign change between each of the plurality of third differences and the respective next difference of the plurality of third differences;

for each determined sign change, determine whether a magnitude of a respective corresponding fourth difference value is greater than a positive third predetermined noise threshold or lower than a negative third predetermined noise threshold;

calculate a total number of the corresponding second difference values having the magnitude greater than the positive third predetermined noise threshold or lower than the negative third predetermined noise threshold; and determine whether the calculated total number is greater than a fourth predetermined noise threshold.

21. Non-transitory, computer-readable storage media storing a set of instructions that, when executed, cause processing circuitry to:

determine an R-wave of a cardiac signal, the cardiac signal being sensed by a plurality of electrodes of an implantable medical device comprising a housing, and sensing circuitry disposed within the housing configured to sense the cardiac signal based on electrical activity of a heart of a patient via the plurality of electrodes;

determine one or more RR intervals, wherein the one or more RR intervals comprise at least one of a previous RR interval associated with the determined R-wave or a current RR interval associated with the determined R-wave;

determine a T-wave of the cardiac signal based on at least a portion of the one or more RR intervals of the cardiac signal;

determine at least one of a QT interval or a QTc interval based on the determined T-wave and the determined R-wave; and at least one of predict or detect an abnormal cardiac rhythm based at least in part on the at least one of the QT interval or the corrected QT interval.

* * * * *